US005135563A

United States Patent [19]

Hiratsuka et al.

[11] Patent Number: 5,135,563

[45] Date of Patent: Aug. 4, 1992

[54] PYRIMIDINE DERIVATIVE

[75] Inventors: Mitsunori Hiratsuka, Toyonaka; Naonori Hirata, Sanda; Kazuo Saitoh; Hideyuki Shibata, both of Toyonaka, all of Japan

[73] Assignee: Sumitomo Chemical Company, Limited, Osaka, Japan

[21] Appl. No.: 726,218

[22] Filed: Jul. 5, 1991

[30] Foreign Application Priority Data

Jul. 5, 1990 [JP] Japan ................................. 2-178967
Apr. 26, 1991 [JP] Japan ................................. 3-124816

[51] Int. Cl.$^5$ .................. C07D 401/12; C07D 239/34; C07D 239/52; A01N 43/54

[52] U.S. Cl. ............................................ 71/92; 71/90; 71/91; 544/300; 544/301; 544/310; 544/312; 544/316; 544/295; 544/296; 544/54; 544/55; 544/58.2; 544/58.6; 544/96; 544/123; 540/470; 540/467; 540/488; 540/544; 540/553; 540/575; 540/601

[58] Field of Search ............... 71/90, 91, 92; 544/300, 544/312, 295, 55, 96; 540/470, 544, 601

[56] References Cited

U.S. PATENT DOCUMENTS 4,248,619 2/1981 Serban et al. .......................... 71/92

FOREIGN PATENT DOCUMENTS

89A39549 8/1989 Australia .
0223406 5/1987 European Pat. Off. .
0249707 12/1987 European Pat. Off. .
0249708 12/1987 European Pat. Off. .
0287072 10/1988 European Pat. Off. .
0287079 10/1988 European Pat. Off. .
0314623 5/1989 European Pat. Off. .
0315889 5/1989 European Pat. Off. .
0321846 6/1989 European Pat. Off. .
0335409 10/1989 European Pat. Off. .
0336494 10/1989 European Pat. Off. .
0346789 12/1989 European Pat. Off. .
0360163 3/1990 European Pat. Off. .
0372329 6/1990 European Pat. Off. .
0374839 6/1990 European Pat. Off. .
0402751 6/1990 European Pat. Off. .
3910635 4/1989 Fed. Rep. of Germany .
3927382 8/1989 Fed. Rep. of Germany .
54-117486 9/1979 Japan .
63-258462 10/1988 Japan .
63-258463 10/1988 Japan .
63-258467 10/1988 Japan .
1-290671 11/1989 Japan .
2-56469 2/1990 Japan .
3-31266 2/1991 Japan .
3-52873 3/1991 Japan .
3-128362 5/1991 Japan .
2237570 10/1990 United Kingdom .

*Primary Examiner*—John M. Ford
*Attorney, Agent, or Firm*—Stevens, Davis, Miller & Mosher

[57] ABSTRACT

The present invention relates to a pyrimidine derivative having the formula

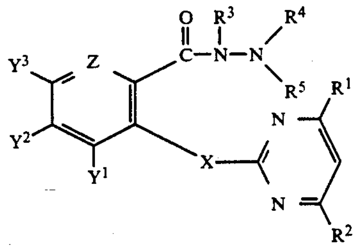

(wherein the variables are defined in the full text of the patent), a method for producing the same, and its use as a herbicide.

13 Claims, No Drawings

PYRIMIDINE DERIVATIVE

The present invention relates to a novel pyrimidine derivative, a method for producing the same, its use as a herbicide and an intermediate of the same.

European Patent Application No. 0223 406A1, 0249 708A1, 0249 707A1, etc. disclose that pyrimidine derivatives can be used as an active ingredient for herbicides.

However, these compounds are not always said to be satisfactory because they are insufficient in herbicidal activity.

On the other hand, a large number of herbicides for crop lands or non-crop lands are now in use. However, there are many kinds of weeds to be controlled and generation of the weeds extends over a long period of time, so that development of herbicides having a higher herbicidal activity and a broader herbicidal spectrum than before is being desired. Further, in recent years, no-till cultivation has been carried out for the purposes of saving labor, extending cultivation period, preventing soil erosion, etc. Therefore, it is being much desired to develop herbicides having both a high post-emergence herbicidal activity against weeds and pre-emergence herbicidal activity, their excellent residual activity at high level, and a high selectivity to the undesired weeds as compared with the desired crops.

In view of the situation like this, the present inventors have extensively studied, and as a result, have found that pyrimidine derivatives represented by the following formula (I) are compounds having an excellent herbicidal activity and having few foregoing defects, and that some of the derivatives have a high selectivity to the undesired weeds as compared with the desired crops. That is, the pyrimidine derivative can control the undesired weeds widely generated in crop lands or non-crop lands at low dosage rates, has a broad herbicidal spectrum and also can safely be used for no-till cultivation. The present invention is based on this finding.

According to the present invention, there are provided a pyrimidine derivative having the formula (hereinafter present compound),

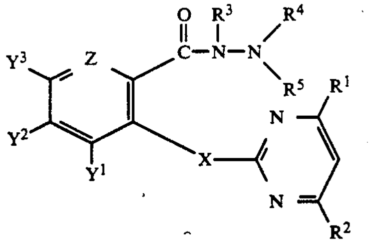

(I)

wherein each of $R^1$ and $R^2$, which may be the same or different, is $C_1$–$C_6$ alkyl, $C_1$–$C_6$ alkoxy, halo $C_1$–$C_6$ alkoxy or halogen;

$R^3$ is hydrogen, $C_1$–$C_6$ alkyl, phenyl or phenyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl, nitro and halogen;

each of $R^4$ and $R^5$, which may be the same or differnt, is hydrogen, $C_1$–$C_6$ alkyl, halo $C_1$–$C_6$ alkyl, phenyl, phenyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl, nitro and halogen, benzyl, pyridyl, pyridyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl, nitro and halogen, quinolinyl, quinolinyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl, nitro and halogen, $C_1$–$C_6$ alkylcarbonyl, $C_1$–$C_6$ alkoxycarbonyl, and

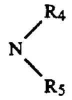

may be

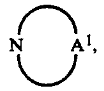

wherein $A^1$ is $C_4$–$C_7$ alkylene, $C_4$–$C_7$ alkylene substituted with $C_1$–$C_6$ alkyl, a group of the formula, $$-(CH_2)_q-A^2-(CH_2)_r-,$$

wherein $A^2$ is S, O,

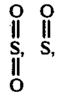

$NR^9$,

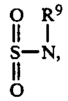

wherein $R^9$ is hydrogen, $C_1$–$C_6$ alkyl, q and r are integer and satisfy the inequalities, $3 \leqq q+r \leqq 6$, $q \geqq 1$, $r \geqq 1$, or a group of the formula, $$-(CH_2)_q-A^2-(CH_2)_r-,$$

substituted with $C_1$–$C_6$ alkyl wherein q, r and $A^2$ are as defined above; or a group of the formula,

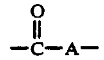

wherein A is $C_2$–$C_4$ alkylene or $C_2$–$C_4$ alkylene substituted with $C_1$–$C_6$ alkyl, or a group of the formula,

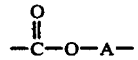

wherein

- A is as defined above;
- X is oxygen or sulfur;
- Z is nitrogen or $CY^4$;
- each of $Y^1$, $Y^2$ and $Y^3$, which may be the same or different, is hydrogen, halogen, $C_1$–$C_6$ alkyl or $C_1$–$C_6$ alkoxy; and
- $Y^4$ is hydrogen, hydroxyl, mercapto, nitro, halogen, $C_1$–$C_6$ alkyl, $C_2$–$C_6$ alkenyl, $C_2$–$C_6$ alkynyl, $C_1$–$C_6$ alkoxy, $C_3$–$C_6$ alkenyloxy, $C_3$–$C_6$ alkynyloxy, halo $C_1$–$C_6$ alkyl, halo $C_2$–$C_6$ alkenyl, halo $C_2$–$C_6$ alkynyl, halo $C_1$–$C_6$ alkoxy, halo $C_3$–$C_6$ alkenyloxy, halo $C_3$–$C_6$ alkynyloxy, $C_1$–$C_6$ alkoxy $C_1$–$C_6$ alkyl, $C_3$–$C_6$ alkenyloxy $C_1$–$C_6$ alkyl, $C_3$–$C_6$ alkynyloxy $C_1$–$C_6$ alkyl, cyano, formyl, carboxyl, $C_1$–$C_6$ alkoxycarbonyl, $C_3$–$C_6$ alkenyloxycarbonyl, $C_3$–$C_6$ alkynyloxycarbonyl, phenyl, phenyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen, phenoxy, phenoxy substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen, phenylthio, phenylthio substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen, benzyloxy, benzyloxy substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen, benzylthio, benzylthio substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen,

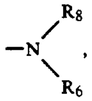

wherein each of $R^8$ and $R^6$, which may be the same or different, is hydrogen, $C_1$–$C_6$ alkyl, $C_3$–$C_6$ alkenyl or $C_3$–$C_6$ alkynyl,

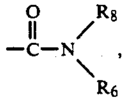

wherein $R^8$ and $R^6$ are as defined above,

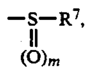

wherein $R^7$ is $C_1$–$C_6$ alkyl, $C_3$–$C_6$ alkenyl or $C_3$–$C_6$ alkynyl and m is an integer of 0, 1 or 2,

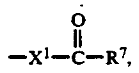

wherein $X^1$ is oxygen or sulfur, and $R^7$ is as defined above, or

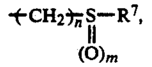

wherein $R^7$ and m are as defined above, and n is an integer of from 1 to 4; a method for producing the pyrimidine derivative (I) which comprises the steps of (i) reacting a carboxylic acid derivative having the formula (II),

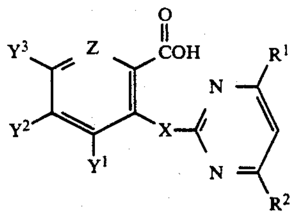

(II)

wherein X, Z, $Y^1$, $Y^2$, $Y^3$, $R^1$ and $R^2$ are as defined above, with an acid-halogenating agent or an active esterifying agent to obtain a reaction product; and (ii) reacting the reaction product with a hydrazine derivative having the formula,

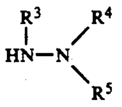

(III)

wherein $R^3$, $R^4$ and $R^5$ are as defined above;

a herbicidal composition which comprises as an active ingredient a herbicidally effective amount of the pyrimidine derivative described above, and an inert carrier or a diluent;

a method for controlling undesirable weeds, which comprises applying the above herbicidal composition to an area where undesirable weeds grow or are likely to grow; and a use of the pyrimidine derivative as a herbicide.

In the formula (I), examples of the $C_1$–$C_6$ alkyl group include methyl, ethyl, n-propyl, isopropyl, n-butyl, sec-butyl, tert-butyl, n-hexyl, etc; examples of the $C_1$–$C_6$ alkoxy group include methoxy, ethoxy, n-propoxy, isopropoxy, n-butoxy, hexyloxy, etc; and examples of the $C_1$–$C_6$ alkoxycarbonyl group include methoxycarbonyl, ethoxycarbonyl, n-butoxycarbonyl, hexyloxycarbonyl, etc.

The hetero atom in the formula (I) includes nitrogen, oxygen and sulfur.

The halogen atom in the formula (I) includes fluorine, chlorine, bromine and iodine.

Examples of the halo $C_1$–$C_6$ alkyl group include fluoromethyl, difluoromethyl, trifluoromethyl, 2-chloroethyl, 3-bromopropyl, etc.

Examples of the alkylcarbonyl group include methylcarbonyl, ethylcarbonyl, n-butylcarbonyl, and hexylcarbonyl.

Examples of $C_4$–$C_7$ alkylene and $C_4$–$C_7$ alkylene substituted with $C_1$–$C_6$ alkyl include tetramethylene, pentamethylene, hexamethylene, 1,4-dimethyltetramethylene, 1,5-dimethylpentamethylene, 1-methylpentamethylene, 2-methylpentamethylene, 2-ethylpentamethylene, 2-butylpentamethylene, and 2-hexyltetramethylene, Examples of $C_3$–$C_6$ alkylene containing a hetro atom and $C_3$–$C_6$ alkylene containing a hetero atom and substituted with $C_1$–$C_6$ alkyl include:

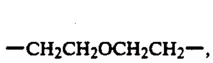, 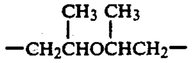

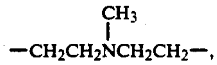, 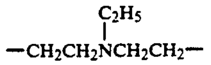

-continued

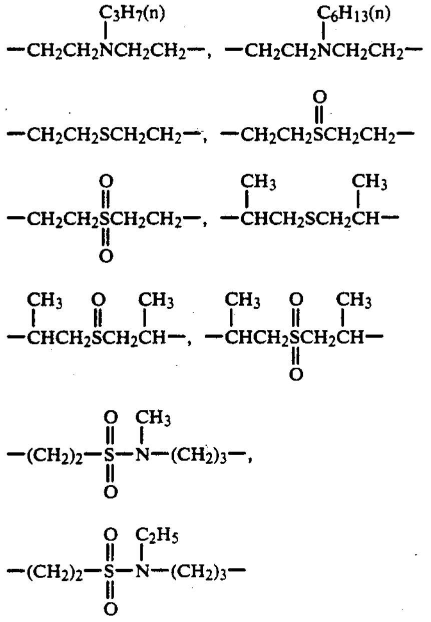

Examples of $C_2$–$C_4$ alkylene and $C_2$–$C_4$ alkylene substituted with $C_1$–$C_6$ alkyl as A include ethylene, trimethylene, tetramethylene, 1,4-dimethyltetramethylene, 1-methyltrimethylene, 2-ethyltrimethylene, and 2-methyltetramethylene.

When phenyl or a substituted phenyl group is selected as $R^3$, $R^4$ and $R^5$, the examples thereof include phenyl, 2-methylphenyl, 3-ethylphenyl, 4-hexylphenyl, 2,6-dimethylphenyl, 3-methoxyphenyl, 4-isopropoxyphenyl, 3-hexyloxyphenyl, 2-trifluoromethylphenyl, 3-difluoromethylphenyl, 2-methoxycarbonylphenyl, 2-ethoxycarbonylphenyl, 2-n-propoxycarbonylphenyl, 2-hexyloxycarbonylphenyl, 2-fluorophenyl, 2-chlorophenyl, 3-bromophenyl, 2,4-dichlorophenyl, nitrophenyl etc.

When a halo $C_1$–$C_6$ alkoxy group is selected as $R^1$ or $R^2$, the examples thereof include fluoromethoxy, difluoromethoxy, trifluoromethoxy, etc.

When a $C_2$–$C_6$ alkenyl group is selected as $Y^4$, the examples thereof include vinyl, allyl, 1-butenyl, 2-butenyl, 3-butenyl, 3-pentenyl, 2-pentenyl, 2-hexenyl, etc.

When a $C_2$–$C_6$ alkynyl group is selected as $Y^4$, the examples thereof include ethynyl, propargyl, 1-butynyl, 2-butynyl, 2-pentynyl, 3-pentynyl, 2-hexynyl, etc.

When a $C_3$–$C_6$ alkenyloxy group is selected as $Y^4$, the examples thereof include allyloxy, 2-butenyloxy, 3-butenyloxy, 2-hexenyloxy, etc.

When a $C_1$–$C_6$ alkynyloxy group is selected as $Y^4$, the examples thereof include propargyloxy, 2-butynyloxy, 3-butynyloxy, 2-hexynyloxy, etc.

When a halo $C_2$–$C_6$ alkenyl group is selected as $Y^4$, the examples thereof include 1-chlorovinyl, 3-chloroallyl, 5-bromo-2-pentenyl, 6-iodo-2-hexenyl, 5,5,5-trifluoro-2-pentenyl, etc.

When a halo $C_2$–$C_6$ alkynyl group is selected as $Y^4$, the examples thereof include 2-iodoethynyl, 5-bromo-2-pentynyl, 6-iode-2-hexynyl, 5,5,5-trifluoro-2-pentynyl, etc.

When a halo $C_1$–$C_6$ alkoxy group is selected as $Y^4$, the examples thereof include fluoromethoxy, difluoromethoxy, trifluoromethoxy, 1,1,2,2-tetrafluoroethoxy, etc.

When a halo $C_3$–$C_6$ alkenyloxy group is selected as $Y^4$, the examples thereof include 3-chloroallyloxy, 5-bromo-2-pentenyloxy, 6-iodo-2-hexenyloxy, 5,5,5-trifluoro-2-pentenyloxy, etc.

When a halo $C_3$–$C_6$ alkynyloxy group is selected as $Y^4$, the examples thereof include 5-bromo-2-pentynyloxy, 5-chloro-2-pentynyloxy, 1-iodo-2-hexynyloxy, 5,5,5-trifluoro-2-pentynyloxy, 3-iodopropargyloxy, etc.

When a $C_1$–$C_6$ alkoxy $C_1$–$C_6$ alkyl group is selected as $Y^4$, the examples thereof include methoxymethyl, ethoxymethyl, 2-methoxyethyl, 4-n-propoxybutyl, 2-n-butoxyethyl, 6-hexyloxyhexyl, etc.

When a $C_1$–$C_6$ alkenyloxy $C_1$–$C_6$ alkyl group is selected as $Y^4$, the examples thereof include allyloxymethyl, 2-allyloxyethyl, 4-allyloxybutyl, 3-(2-butenyloxy)propyl, 6-(hexenyloxy)hexyl, etc.

When a $C_3$–$C_6$ alkynyloxy $C_1$–$C_6$ alkyl group is selectd as $Y^4$, the examples thereof include propargyloxymethyl, 2-propargyloxyethyl, 4-propargyloxybutyl, 3-(2-butynyloxy)propyl, 6-(2-hexynyloxy)hexyl, etc.

When a $C_3$–$C_6$ alkenyloxycarbonyl group is selected as $Y^4$, the examples thereof include allyloxycarbonyl, 2-butenyloxycarbonyl, 3-butenyloxycarbonyl, 2-hexenyloxycarbonyl, etc.

When a $C_3$–$C_6$ alkynyloxycarbonyl group is selected as $Y^4$, the examples thereof include propargyloxycarbonyl, 2-butynyloxycarbonyl, 3-butynyloxycarbonyl, 2-hexynyloxycarbonyl, etc.

When phenoxy or a substituted phenoxy group is selectd as $Y^4$, the examples thereof include phenoxy, 2-methylphenoxy, 3-ethylphenoxy, 4-hexylphenoxy, 2,6-dimethylphenoxy, 3-methoxyphenoxy, 4-isopropoxyphenoxy, 3-hexyloxyphenoxy, 2-trifluoromethylphenoxy, 3-difluoromethylphenoxy, 2-methoxycarbonylphenoxy, 2-ethoxycarbonylphenoxy, 2-n-propoxycarbonylphenoxy, 2-hexyloxycarbonylphenoxy, 2-fluorophenoxy, 2-chlorophenoxy, 3-bromophenoxy, 2,4-dichlorophenoxy, etc.

When phenyl or a substituted phenyl group is selected as $Y^4$, the examples thereof include phenyl, 2-methylphenyl, 3-ethylphenyl, 4-hexylphenyl, 2,6-dimethylphenyl, 3-methoxyphenyl, 4-isopropoxyphenyl, 3-hexyloxyphenyl, 2-trifluoromethylphenyl, 3-difluoromethylphenyl, 2-methoxycarbonylphenyl, 2-ethoxycarbonylphenyl, 2-n-propoxycarbonylphenyl, 2-hexyloxycarbonylphenyl, 2-fluorophenyl, 2-chlorophenyl, 3-bromophenyl, 2,4-dichlorophenyl, etc.

When phenylthio or a substituted phenylthio group is selected as $Y^4$, the examples thereof include phenylthio, 2-methylphenylthio, 3-ethylphenylthio, 4-hexylphenylthio, 2,6-dimethylphenylthio, 3-methoxyphenylthio, 4-isopropoxyphenylthio, 3-hexyloxyphenylthio, 2-trifluoromethylphenylthio, 3-difluoromethylphenylthio, 2-methoxycarbonylphenylthio, 2-ethoxycarbonylphenylthio, 2-n-propoxycarbonylphenylthio, 2-hexyloxycarbonylphenylthio, 2-fluorophenylthio, 2-chlorophenylthio, 3-bromophenylthio, 2,4-dichlorophenylthio, etc.

When benzyloxy or a substituted benzyloxy group is selectd as $Y^4$, the examples thereof include benzyloxy, 2-methylbenzyloxy, 3-ethylbenzyloxy, 4-hexylbenzyloxy, 2,6-dimethylbenzyloxy, 3-methoxybenzyloxy, 4-isopropoxybenzyloxy, 3-hexyloxybenzyloxy, 2-trifluoromethylbenzyloxy, 3-difluoromethylbenzyloxy, 2-methoxycarbonylbenzyloxy, 2-ethoxycarbonylbenzyloxy, 2-n-propoxycarbonylbenzyloxy, 2-hexyloxycarbonylbenzyloxy 2-fluorobenzyloxy, 2-chlorobenzyloxy, 3-bromobenzyloxy, 2,4-dichlorobenzyloxy, etc.

When benzylthio or a substituted benzylthio group is selected as $Y^4$, the examples thereof include benzylthio, 2-methylbenzylthio, 3-ethylbenzylthio, 4-hexylbenzylthio, 2,6-dimethylbenzylthio, 3-methoxybenzylthio, 4-isopropoxybenzylthio, 3-hexyloxybenzylthio, 2-trifluoromethylbenzylthio, 3-difluoromethylbenzylthio, 2-methoxycarbonylbenzylthio, 2-ethoxycarbonylbenzylthio, 2-n-propoxycarbonylbenzylthio, 2-hexyloxycarbonylbenzylthio, 2-fluorobenzylthio, 2-chlorobenzylthio, 3-bromobenzylthio, 2,4-dichlorobenzylthio, etc.

When a $C_3$–$C_6$ alkenyl group is selected as $R^8$, $R^6$ or $R^7$, the examples thereof include allyl, 1-butenyl, 2-butenyl, 3-butenyl, 2-pentenyl, 3-pentenyl, 2-hexenyl, etc.

When a $C_3$–$C_6$ alkynyl group is selected as $R^8$, $R^6$ or $R^7$, the examples thereof include propargyl, 1-butynyl, 2-butynyl, 2-pentynyl, 3-pentynyl, 2-hexynyl, etc.

In the compound of the formula (I), the substituents $R^1$ and $R^2$, which may be the same or different, are preferably $C_1$–$C_6$ alkoxy, and more preferably, both of them are methoxy.

Z is preferably nitrogen or CY5 wherein Y5 is hydrogen, halogen, a halo $C_1$–$C_6$ alkyl group, a $C_1$–$C_6$ alkyl group, a $C_1$–$C_6$ alkoxy group, phenyl, phenyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl or halogen. More preferably, Z is nitrogen or $CY^5$ in which $Y^5$ is hydrogen or halogen. Most preferably Z is $CY^5$ and $Y^5$ is halogen.

$Y^1$ *and* $Y^2$, which may be the same or different, are preferably a hydrogen atom or a fluorine atom.

$Y^3$ is preferably hydrogen, fluorine or a $C_1$–$C_6$ alkoxy group. Specific examples of the pyrimidine derivative of the present invention include:

(a)

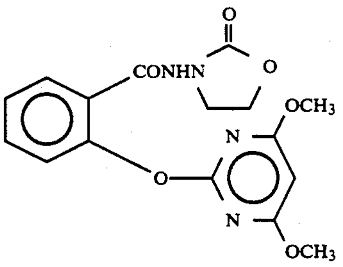

3-{6-(4,6-dimethoxypyrimidin-2-yl)oxybenzoyl}amino-2-oxazolidinone, and (b)

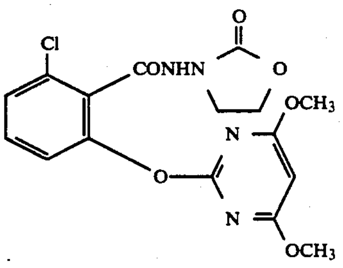

3-{2-chloro-6-(4,6-dimethoxypyrimidin-2-yl)oxybenzoyl}-amino-2-oxazolidinone.

Compound (a) has a good selectivity to undesired weeds as compared with soybean in soil treatment.

The present compound having the formula (I) in which Z is CCl, CF or CBr and each of $R^1$ and $R^2$ is methoxy has an excellent herbicidal activity and a good selectivity to undesired weeds as compared with cotton.

A method for producing the present compound is as follows.

The present compound can be produced by reacting a compound represented by the formula (II), (II)

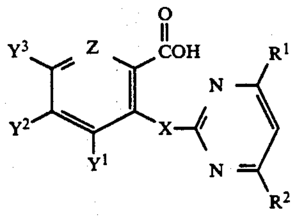

wherein $R^1$, $R^2$, X, $Y^1$, $Y^2$, $Y^3$ and Z are as defined above, with an acid-halogenating agent or an active esterifying agent (hereinafter reaction (i)), and reacting the resulting reaction product with a hydrazine derivative represented by the formula (III), (III)

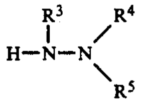

wherein $R^3$, $R^4$ and $R^5$ are as defined above (hereinafter reaction (ii).

In the above reaction (i), specific examples of the acid-halogenating agent are thionyl chloride, thionyl bromide, phosphorus trichloride, phosphorus tribromide, phosphorus pentachloride, phosphorus oxychloride, phosgene, oxalic acid dichloride, etc. Specific examples of the active esterifying agent are N,N'-disubstituted carbodiimides such as N,N'-dicyclohexylcarbodiimide, N,N'-diisopropylcarbodiimide, 1-ethyl-3-(3-dimethylaminopropyl)carbodiimide hydrochloride, etc.; arylsulfonyl chlorides such as 2,4,6-trimethylbenzenesulfonyl chloride, 2,4,6-triisopropylbenzenesulfonyl chloride, etc.; N,N'-carbonyldiimidazole; diphenylphosphorylazide; N-ethoxycarbonyl-2-ethoxy-1,2-dihydroquinoline; N-ethyl-2'-hydroxybenzisoxazolium trifluoroborate; N-ethyl-5-phenylisoxazolium-3'-sulfonate; etc.

By this reaction, a compound represented by the formula (IV), (IV)

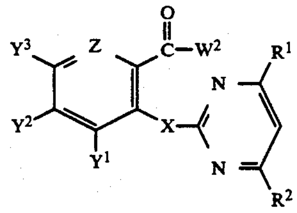

wherein $R^1$, $R^2$, X, $Y^1$, $Y^2$, $Y^3$ and Z are as defined above, is produced in the reaction system.

In the above formula (IV), a substituent $W^2$ represents a halogen atom when the acid-halogenating agent was used; $W^2$ represents an N,N'-disubstituted-2-isoureido group when N,N'-disubstituted carbodiimide was used as the active esterifying agent; $W^2$ represents an arylsulfonyloxy group when arylsulfonyl chloride was used as said agent; $W^2$ represents an imidazolyl group when N,N'-carbonyldiimidazole was used as said agent; $W^2$ represents an azide group when diphenylphosphorylazide was used as said agent; $W^2$ represents an ethoxycarbonyloxy group when N-ethoxycarbonyl-2-ethoxy-1,2-dihydroquinoline was used as said agent; $W^2$ represents a 3-(N-ethylaminocarbonyl)-2-hydroxyphenoxy group when N-ethyl-2'-hydroxybenzisoxazolium trifluoroborate was used as said agent; and $W^2$ represents a group

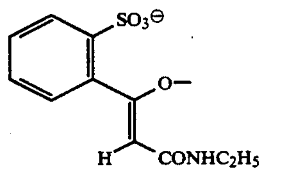

when N-ethyl-5-phenylisoxazolium-3'-sulfonate was used as said agent.

In the reaction system, $W^2$ can also take a form of acid anhydride containing the moiety represented by the formula,

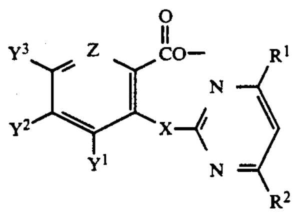

wherein $R^1$, $R^2$, X, $Y^1$, $Y^2$, $Y^3$ and Z are as defined above.

The amount of the foregoing acid-halogenating agent or active esterifying agent used is usually 1 to 10 equivalents based on 1 equivalent of the compound represented by the formula (II).

The amount of the hydrazine derivative of the formula (III) used is usually 1 to 5 equivalents based on 1 equivalent of the compound represented by the formula (II).

The reactions (i) and (ii) can also be carried out, if necessary, in the presence of a base. Such a base includes organic bases (e.g. 1-methylimidazole, 3-nitro-1H-1,2,4-triazole, 1H-tetrazole, 1H-1,2,4-triazole, imidazole, pyridine, triethylamine) and inorganic bases (e.g. potassium carbonate). The amount of the base used is usually 1 to 20 equivalents based on 1 equivalent of the compound represented by the formula (II).

The reactions (i) and (ii) are usually carried out in the presence of an inert solvent. Such a solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. N,N-dimethylformamide), sulfur compounds (e.g. dimethyl sulfoxide, sulfolane) and the mixtures thereof.

Generally, the reaction temperature usually ranges from 0° C. to the boiling point of the solvent in any of the reactions (i) and (ii). The reaction time usually ranges from 1 to 24 hours for each reaction, and from about 1 to about 48 hours through the reactions (i) and (ii).

After completion of the reaction, the reaction solution may be after-treated as usual. That is, water is added to the solution which is then extracted with an organic solvent and concentrated, and if necessary, the product obtained is subjected to the chromatography, distillation, recrystallization, etc. Thus, the desired present compound can be obtained.

The compound represented by the formula (2) can be produced according to EP 0 223 406 A1, etc.

Compound (I) includes its stereo isomers having a herbicidal activity.

The present compounds (I) have an excellent herbicidal activity and some of them have an excellent selectivity to the undesired weeds as compared with the desired crops.

That is, the present compound, when used for foliar treatment and soil treatment in upland fields, exhibits a herbicidal activity against a wide variety of undesired weeds. Also, the present compound (I), when used for flooding treatment in paddy fields, exhibits a herbicidal activity against a wide variety of undesired weeds.

The present compound (I) can control a wide range of weeds generated in crop lands or non-crop lands, can be applied in low dosage rates, has a broad herbicidal spectrum and also can safely be used for no-till cultivation in soybean fields, peanut fields, corn fields, etc.

As weeds which can be controlled by the present compound, there are mentioned for example broad-leaved weeds such as wild buckwheat (*Polygonum convolvulus*), pale smartweed (*Polyqonum lapathifolium*), common purslane (*Portulaca oleracea*), chickweed (*Stellaria media*), common lambsquarters (*Chenopodium album*), redroot pigweed (*Amaranthus retroflexus*), radish (*Raphanus sativus*), wild mustard (*Sinapis arvensis*), shepherds purse (*Capsella bursa-pastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), cleavers (*Galium aparine*), ivyleaf morningglory (*Ipomoea hederacea*), tall morningglory (*Ipomoea purpurea*), field bindweed (*Convolvulus arvensis*), red deadnettle (*Lamium purpureum*), henbit (*Lamium amplexicaure*), jimsonweed (*Datura stramonium*), black nightshade (*Solanum niqrum*), birdseye speedwell (*Veronica persica*), cocklebur (*Xanthium strumarium*), sunflower (*Helianthus annuus*), scentless chamomile (*Matricaria perforata*), corn marigold (*Chrvsanthemum segetum*), etc.; Gramineae weeds such as Japanese millet (*Echinochloa frumentacea*), barnyardgrass (*Echinochloa crus-qalli*), green foxtail (*Setaria viridis*), giant foxtail (*Setaria faberi*), large crabgrass (*Diqitaria sanquinalis*), annual bluegrass (*Poa annua*), blackgrass (*Alopecurus myosuroides*), oat (*Avena sativa*), wild oat (*Avena fatua*), johnsongrass (*Sorqhum halepense*), quackgrass (*AqropVron repens*), downy brome (*Bromus tectorum*), bermudagrass (*Cynodon dactylon*), etc.; Commelinaceae weeds such as dayflower (*Commelina communis*), etc.; and Cyperaceae weeds such as rice flatsedge (*Cyperus iria*), purple nutsedge (*Cyperus rotundus*), etc. In addition, some of the present compounds give such no phytotoxicity as becoming a problem to main crops such as corn, wheat, barley, rice, soybean, cotton, beet, etc.

In flooding treatment in paddy fields, the present compounds exhibit a herbicidal activity against gramineous weeds such as barnyardgrass (*Echinochloa oryzicola*), etc.; broad-leaved weeds such as false pimpernel (*Lindernia procumbens*), indian toothcup (*Rotala indica*), waterwort (*Elatine triandra*), Ammannia multiflora, etc.; Cyperaceae weeds such as smallflower umbrellaplant (*Cyperus difformis*), bulrush (*Scirpus juncoides*), slender spikerush (*Eleocharis acicularis*), water nutgrass (*Cyperus serotinus*), etc.; monochoria (*Monochoria vaqinalis*), arrowhead (*Saqittaria pygmaea*), etc.

When the present compound (I) is used as an active ingredient for herbicides, it is usually formulated before use into emulsifiable concentrates, wettable powders, suspension formulations, granules, water-dispersible granules, etc. by mixing the present compound (I) with solid carriers, liquid carriers, surface active agents or other auxiliaries for formulation.

The content of the compound (I) as an active ingredient in these preparations is normally within a range of about 0.001 to 90% by weight, preferably of about 0.003 to 80% by weight.

Examples of the solid carriers are fine powders or granules of kaolin clay, attapulgite clay, bentonite, terra alba, pyrophyllite, talc, diatomaceous earth, calcite, walnut shell powders, urea, ammonium sulfate and synthetic hydrated silicon dioxide, etc.

Examples of the liquid carriers are aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (soybean oil, cotton seed oil), dimethyl sulfoxide, N,N-dimethylformamide, acetonitrile, water, etc.

Examples of the surface active agents used for emulsification, dispersion or spreading, etc. are anionic surface active agents such as salts of alkyl sulfates, alkylsulfonates, alkylarylsulfonates, dialkyl sulfosuccinates, salts of polyoxyethylene alkylaryl ether phosphoric acid esters, etc., and nonionic surface active agents such as polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc.

Examples of the other auxiliaries for formulation are lignosulfonates, alginates, polyvinyl alcohol, gum arabic, CMC (carboxymethyl cellulose), PAP (isopropyl acid phosphate), etc.

The present compound (I) is usually formulated into an appropriate formulation and used in soil treatment, foliar treatment or flooding treatment before or after emergence of weeds. The soil treatment includes soil surface treatment and soil incorporation treatment. The foliar treatment includes, in addition to the treatments of plants mentioned above, direct treatment in which the formulation is applied only to weeds so as to prevent the formulation from adhering to crops.

The herbicidal activity of the present compound (I) can be expected to be increased by using the compound in mixture with other herbicides. Further, the present compound (I) can also be used in mixture with insecticides, acaricides, nematocides, fungicides, plant growth regulators, fertilizers, soil improvers, etc.

The present compound (I) can be used as an active ingredient for herbicides used in paddy fields, ridges of paddy fields, plowed fields, fields other than plowed fields, orchards, pastures, turfs, forests and fields other than agricultural fields, etc.

When the present compound (I) is used as an active ingredient for herbicides, the dosage rate varies depending upon the weather conditions, preparation forms, when, how and where the treatment is carried out, weeds species to be controlled, crops species to be protected, etc. Usually, however, the dosage rate is from 0.003 grams to 500 grams of the active ingredient per are, preferably from 0.01 grams to 100 grams of the active ingredient per are.

The herbicidal composition of the invention formulated in the form of an emulsifiable concentrate, a wettable powder or a suspension formulations may ordinarily be employed after diluting it with water at a volume of about 1 to 10 liters per are. If necessary, auxiliaries such as a spreading agent are added to the water. The granules are usually applied as they are without being diluted.

Examples of the spreading agent are, in addition to the foregoing surface active agents, substances such as polyoxyethylene resin acids (esters), lignosulfonates, abietates, dinaphthylmethanedisulfonates, paraffin, etc.

The present invention will be illustrated in more detail with reference to the following production examples, formulation examples and test examples, which are not however to be interpreted as limiting the invention thereto.

First, production examples for the present compound (I) are shown.

PRODUCTION EXAMPLE 1

1.10 Gram of 2-(4,6-dimethoxypirimidin-2-yl)oxybenzoic acid was dissolved in 10 ml of tetrahydofuran, and 0.77 g of N,N'-carbonyldimidazole was added. After stirring at room temperature for 20 minutes, the reaction solution was cooled to 0° to 5° C. 0.72 Gram of hydrazine monohydrate was added with keeping this temperature. After stirring at 0° to 5° C. for 30 minutes, the reaction solution was pourd into water, and extracted with ethyl acetate. The organic layer was washed with saturated sodium chloride solution twice and dried over anhydrous magnesium sulfate. The solvent was removed under reduced pressure. The residue was washed with diethylether to obtain 0.95 g of 2-(4,6-dimethoxypirimidin-2-yl)oxybenzohydrazide [present compound (1)].

PRODUCTION EXAMPLE 2

1.24 Grams of 2-chloro-6-(4,6-dimethoxypyrimidin-2-yl)oxybenzoic acid was dissolved in 20 ml of N,N-dimethylformamide. To the solution were added 1.20 g of 3-amino-2-oxazolidinone sulfate, 0.67 g of triethylamine, 1.82 g of 2,4,6-triisopropylbenzenesulfonyl chloride and 0.98 g of 1-methylimidazole. The resulting solution was stirred at room temperature for 3 hours. The reaction solution was poured into water and extracted with ethyl acetate. The organic layer separated therefrom was washed with water and dried over anhydrous magnesium sulfate. The solvent was removed from the dried layer under reduced pressure to obtain a residue. Purifying the residue with thin layer chromatography (silica gel, chloroform/methanol: 9/1 by volume) gave 0.2 g of 3-{2-chloro-6-(4,6-dimethoxypyrimidin-2-yl)oxybenzoyl}amino-2-oxazolidinone (present compound (172)).

PRODUCTION EXAMPLE 3

Using the same procedure as in Production Example 2 starting from 1.16 g of 6-methyl-2-(4,6-dimethoxypyrimidin-2-yl)oxybenzoic acid, 1.20 g of 3-amino-2-oxazolidinone sulfate, 0.67 g of triethylamine, 1.82 g of 2,4,6-triisopropylbenzenesulfonyl chloride and 0.98 g of 1-methylimidazole gives 3-{2-(4,6-dimethoxypyrimidin-2-yl)oxy-6-methylbenzoyl}amino-2-oxazolidinone (present compound (198)).

PRODUCTION EXAMPLE 4

Using the same procedure as in Production Example 2 starting from 1.38 g of 6-trifluoromethyl-2-(4,6-dimethoxypyrimidin-2-yl)oxybenzoic acid, 1.20 g of 3-amino-2-oxazolidinone sulfate, 0.67 g of triethylamine, 1.82 g of 2,4,6-triisopropylbenzenesulfonyl chloride and 0.98 g of 1-methylimidazole gives 3-{2-(4,6-dimethoxypyrimidin-2-yl)oxy-6-trifluoromethylbenzoyl}amino-2-oxazolidinone (present compound (197)).

PRODUCTION EXAMPLE 5

Using the same procedure as in Production Example 2 starting from 1.22 g of 6-methoxy-2-(4,6-dimethoxypyrimidin-2-yl) oxybenzoic acid, 1.20 g of 3-amino-2-oxaxolidinone sulfate, 0.67 g of triethylamine, 1.82 g of 2,4,6-triisopropylbenzenesulfonyl chloride and 0.98 g of 1-methylimidazole gives 3-{2-(4,6-dimethoxypyrimidin-2-yl)oxy-6-methoxybenzoyl}amino-2-oxazolidinone (present compound (199)).

PRODUCTION EXAMPLE 6

Using the same procedure as in Production Example 2 starting from 1.41 g of 6-phenyl-2-(4,6-dimethoxypyrimidin-2-yl)oxybenzoic acid, 1.20 g of 3-amino-2-oxazolidinone sulfate, 0.67 g of triethylamine, 1.82 g of 2,4,6-triisopropylbenzenesulfonyl chloride and 0.98 g of 1-methylimidazole gives 3-{2-(4,6-dimethoxypyrimidin-2-yl)oxy-6-phenylbenzoyl}amino-2-oxazolidinone (present compound (200)).

PRODUCTION EXAMPLE 7

Using the same procedure as in Production Example 2 starting from 1.31 g of 2-chloro-6-(4,6-dimethoxypyrimidin-2-yl)thiobenzoic acid, 1.20 g of 3-amino-2-oxazolidinone sulfate, 0.67 g of triethylamine, 1.82 g of 2,4,6-triisopropylbenzenesulfonyl chloride and 0.98 g of 1-methlimidazole gives 3-{2-chloro-6-(4,6-dimethoxypyrimidin-2-yl) thiobenzoyl}amino-2-oxazolidinone (present compound (202))

PRODUCTION EXAMPLE 8

Using the same procedure as in Production Example 2 starting from 1.31 g of 2-chloro-6-(4,6-dimethoxypyrimidin-2-yl)thiobenzoic acid, 0.87 g of 2,4-difluorophenylhydrazine hydrochloride, 0.67 g of triethylamine, 1.82 g of 2,4,6-triisopropylbenzenesulfonyl chloride and 0.98 g of 1-methlimidazole gives 2-chloro-6-(4,6-dimethoxypyrimidin-2-yl)thiobenzoic acid 2,4-difluorophenyl hydrazide (present compound (204)).

Table 1 illustrates specific examples of the compound (I), which can be produced by using the corresponding starting compounds.

TABLE 1

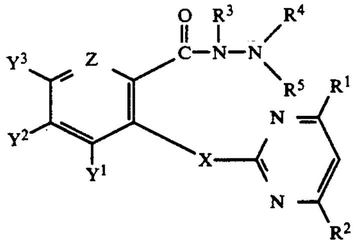

| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (1) | H | H | H | H | H | H | O | CH | $OCH_3$ | $OCH_3$ | m.p. 136–137° C. |
| (2) | H | H | H | H | H | H | O | N | $OCH_3$ | $OCH_3$ | m.p. 179–181° C. (dec.) |
| (3) | H | $CH_3$ | $CH_3$ | H | H | H | O | CH | $OCH_3$ | $OCH_3$ | m.p. 132–133° C. |
| (4) | H | H | H | H | H | H | O | CF | $OCH_3$ | $OCH_3$ | |
| (5) | H | H | H | H | H | H | O | CCl | $OCH_3$ | $OCH_3$ | |
| (6) | H | H | H | H | H | H | O | $COCH_3$ | $OCH_3$ | $OCH_3$ | |
| (7) | H | $CH_3$ | $CH_3$ | H | H | H | O | CBr | $OCH_3$ | $OCH_3$ | |
| (8) | H | $CH_3$ | $CH_3$ | H | H | H | O | $CCH_3$ | $OCH_3$ | $OCH_3$ | |

TABLE 1-continued

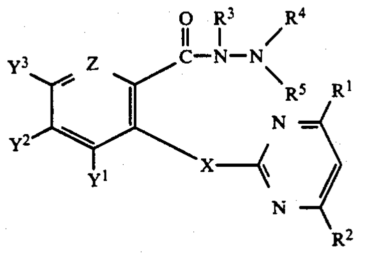

| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (9) | H | $CH_3$ | $CH_3$ | H | H | H | O | $CCF_3$ | $OCH_3$ | $OCH_3$ | |
| (10) | H | $CH_3$ | $CH_3$ | H | H | H | O | $CNO_2$ | $OCH_3$ | $OCH_3$ | |
| (11) | H | $CH_3$ | $CH_3$ | H | H | F | O | CH | $OCH_3$ | $OCH_3$ | |
| (12) | H | $CH_3$ | $CH_3$ | H | H | $OCH_3$ | O | CH | $OCH_3$ | $OCH_3$ | |
| (13) | H | $CH_3$ | $CH_3$ | H | H | F | O | CCl | $OCH_3$ | $OCH_3$ | |
| (14) | H | H | $C_2H_5$ | H | H | H | O | CH | $OCH_3$ | $OCH_3$ | $n_D^{24}$ 1.5332 |
| (15) | H | H | $C_3H_7$(i) | H | H | H | O | CH | $OCH_3$ | $OCH_3$ | m.p. 120–121° C. |
| (16) | H | H | $C_4H_9$(t) | H | H | H | O | CH | $OCH_3$ | $OCH_3$ | m.p. 112.5–113.5° C. |
| (17) | $CH_3$ | H | $CH_3$ | H | H | H | O | CH | $OCH_3$ | $OCH_3$ | $n_D^{19}$ 1.5578 |
| (18) | H | H | $C_4H_9$(t) | H | H | H | O | CCl | Cl | $OCH_3$ | |
| (19) | H | H | $C_4H_9$(t) | H | H | H | O | CCl | $CH_3$ | $CH_3$ | |
| (20) | H | H | $C_6H_{13}$(n) | H | H | H | O | CCl | $OCH_3$ | $OCH_3$ | |
| (21) | $C_2H_5$ | H | $C_2H_5$ | H | H | H | O | CCl | $OCH_3$ | $OCH_3$ | |
| (22) | H | H | $C_4H_9$(t) | H | H | H | S | CCl | $OCH_3$ | $OCH_3$ | |
| (23) | H | $C_2H_5$ | $C_2H_5$ | H | H | H | O | CCl | $OCH_3$ | $OCH_3$ | |
| (24) | H | $C_6H_{13}$(n) | $C_6H_{13}$(n) | H | H | H | O | CCl | $OCH_3$ | $OCH_3$ | |
| (25) | H | $CH_3$ | $CH_2$— 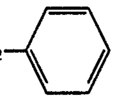 | H | H | H | O | CCl | $OCH_3$ | $OCH_3$ | |
| (26) | H | $C_2H_5$ | $CH_2$— 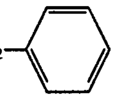 | H | H | H | O | CBr | $OCH_3$ | $OCH_3$ | |
| (27) | H | $C_2H_5$ | $CH_2$— 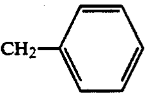 | H | H | H | S | CBr | $OCH_3$ | $OCH_3$ | |
| (28) | H | | $(CH_2)_5$ | H | H | H | O | CH | $OCH_3$ | $OCH_3$ | m.p. 142–143° C. |
| (29) | H | $CH_3$ | $CH_3$ | H | H | H | O | N | $OCH_3$ | $OCH_3$ | 2.60(s, 6H),<br>3.75(s, 6H)<br>5.68(s, 1H)<br>7.47–7.55(m, 2H)<br>8.30–8.40(m, 2H) |
| (30) | H | H | $C_4H_9$(t) | H | H | H | O | N | $OCH_3$ | $OCH_3$ | 1.09(s, 9H),<br>3.76(s, 6H)<br>4.70(bs, 1H),<br>5.70(s, 1H)<br>7.48–7.57(m, 2H)<br>8.42(d×d, 1H, J=4.0, 2.0Hz)<br>9.01(bs, 1H) |
| (31) | H | H | $CH_2CF_3$ | H | H | H | O | CH | $OCH_3$ | $OCH_3$ | m.p. 136.5–137° C. |
| (32) | H | H | $CH_2CF_3$ | H | H | H | O | CF | $OCH_3$ | $OCH_3$ | |
| (33) | H | H | $CH_2CF_3$ | H | H | H | O | CCl | $OCH_3$ | $OCH_3$ | |
| (34) | H | | $(CH_2)_5$ | H | H | H | O | CCl | $OCH_3$ | $OCH_3$ | |
| (35) | H | | $(CH_2)_5$ | H | H | H | O | CBr | $OCH_3$ | $OCH_3$ | |
| (36) | H | | $(CH_2)_5$ | H | H | H | S | CBr | $OCH_3$ | $OCH_3$ | |
| (37) | H | H | 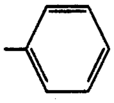 | H | H | H | O | $CCH_3$ | $OCH_3$ | $OCH_3$ | |

TABLE 1-continued

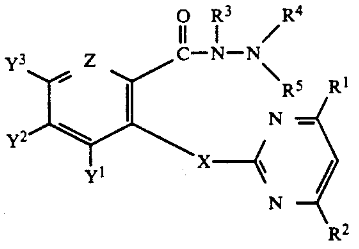

| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (38) | H | H | 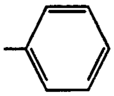 | H | H | H | O | $COCH_3$ | $OCH_3$ | $OCH_3$ | |
| (39) | H | H | 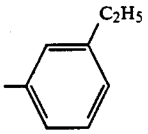 | H | H | H | O | $CC_6H_5$ | $OCH_3$ | $OCH_3$ | |
| (40) | H | H | 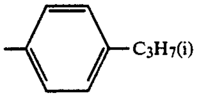 | H | H | H | O | CF | $OCH_3$ | $OCH_3$ | |
| (41) | H | H | 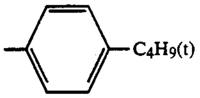 | H | H | H | O | CBr | $OCH_3$ | $OCH_3$ | |
| (42) | H | H | 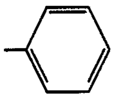 | H | H | H | O | CH | $OCH_3$ | $OCH_3$ | 3.61(s, 6H), 5.71(s, 6H) 6.60–7.43(m, 10H) |
| (43) | H | H | 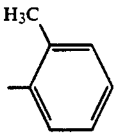 | H | H | H | O | CH | $OCH_3$ | $OCH_3$ | m.p. 145–146° C. |
| (44) | H | H | 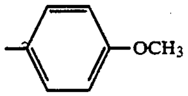 | H | H | H | O | CH | $OCH_3$ | $OCH_3$ | $n_D^{24}$ 1.5398 |
| (45) | H | H | 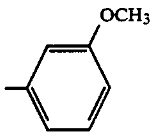 | H | H | H | O | CH | $OCH_3$ | $OCH_3$ | 3.64(s, 3H), 3.74(s, 6H) 5.68(s, 1H) 6.21–8.09(m, 9H) |
| (46) | H | H | 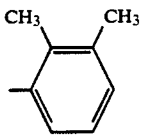 | H | H | H | O | CCl | $OCH_3$ | $OCH_3$ | |

TABLE 1-continued
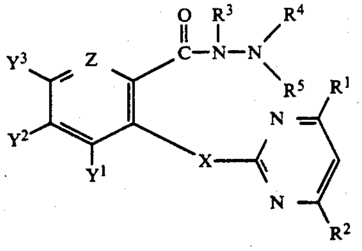
| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (47) | H | H | 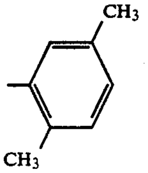 | H | H | H | O | CCl | $OCH_3$ | $OCH_3$ | |
| (48) | H | H | 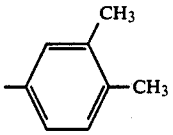 | H | H | H | O | CCl | $OCH_3$ | $OCH_3$ | |
| (49) | H | H | 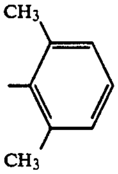 | H | H | H | O | CCl | $OCH_3$ | $OCH_3$ | |
| (50) | H | H | 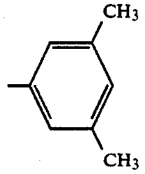 | H | H | H | O | CCl | $OCH_3$ | $OCH_3$ | |
| (51) | H | H | 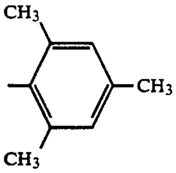 | H | H | H | O | CCl | $OCH_3$ | $OCH_3$ | |
| (52) | H | H | 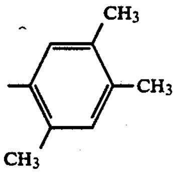 | H | H | H | O | CCl | $OCH_3$ | $OCH_3$ | |
| (53) | H | H | 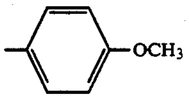 | H | H | H | O | CF | $OCH_3$ | $OCH_3$ | |
| (54) | H | H | 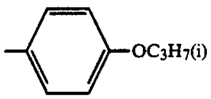 | H | H | H | O | CF | $OCH_3$ | $OCH_3$ | |

TABLE 1-continued

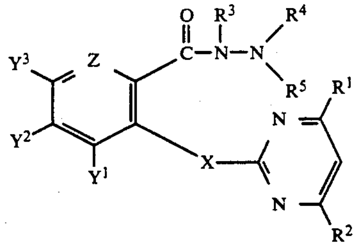

| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (55) | H | H | 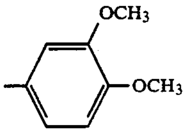 | H | H | H | O | CCl | $OCH_3$ | $OCH_3$ | |
| (56) | H | H | 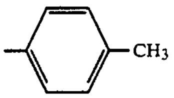 | H | H | H | O | CH | $OCH_3$ | $OCH_3$ | 2.23(S, 3H), 3.74(S, 6H) 5.68(s, 1H) 6.21-8.09(m, 9H) |
| (57) | H | H | 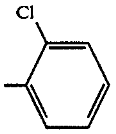 | H | H | H | O | CH | $OCH_3$ | $OCH_3$ | 3.74(s, 6H), 5.67(s, 1H) 6.70-8.10(m, 9H) |
| (58) | H | H | 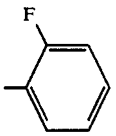 | H | H | H | O | CH | $OCH_3$ | $OCH_3$ | 3.74(s, 6H), 5.67(s, 1H) 6.76-8.36(m, 9H) |
| (59) | H | H | 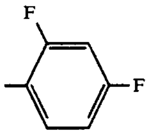 | H | H | H | O | CH | $OCH_3$ | $OCH_3$ | m.p. 112-113° C. |
| (60) | H | H | 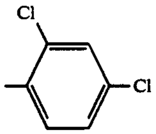 | H | H | H | O | CH | $OCH_3$ | $OCH_3$ | m.p. 164-166° C. (Dec.) |
| (61) | H | H | 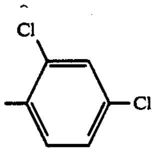 | H | H | H | O | CH | $OCH_3$ | $OCH_3$ | m.p. 139-141° C. |
| (62) | H | H | $C_4H_9$(t) | H | H | H | O | CF | $OCH_3$ | $OCH_3$ | $n_D^{25}$ 1.5242 |
| (63) | H | H | $C_4H_9$(t) | H | H | H | O | CCl | $OCH_3$ | $OCH_3$ | glassy |
| (64) | H | H | 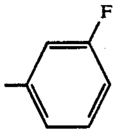 | H | H | H | O | CCl | $OCH_3$ | $OCH_3$ | |

TABLE 1-continued
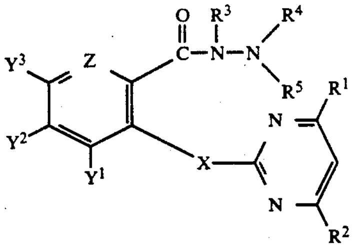
| Compound No. | $R^3$ | $R^4$ | $R^5$ | $Y^1$ | $Y^2$ | $Y^3$ | X | Z | $R^1$ | $R^2$ | Physical properties (m.p., refractive index, $^1H$-NMR ($CDCl_3$, δ)) |
|---|---|---|---|---|---|---|---|---|---|---|---|
| (65) | H | H | 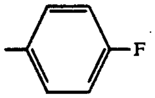 | H | H | H | O | CCl | $OCH_3$ | $OCH_3$ | |
| (66) | H | H | 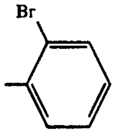 | H | H | H | O | CCl | $OCH_3$ | $OCH_3$ | |
| (67) | H | H | 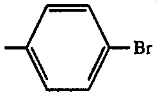 | H | H | H | O | CCl | $OCH_3$ | $OCH_3$ | |
| (68) | H | H | 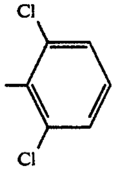 | H | H | H | O | CCl | $OCH_3$ | $OCH_3$ | |
| (69) | H | H | 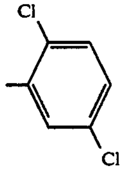 | H | H | H | O | CCl | $OCH_3$ | $OCH_3$ | |
| (70) | H | H | 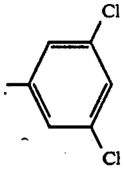 | H | H | H | O | CCl | $OCH_3$ | $OCH_3$ | |
| (71) | H | H | 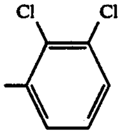 | H | H | H | O | CCl | $OCH_3$ | $OCH_3$ | |
| (72) | H | H | 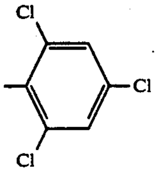 | H | H | H | O | CCl | $OCH_3$ | $OCH_3$ | |

TABLE 1-continued

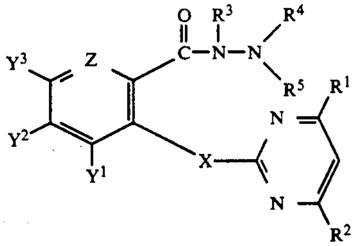

| Compound No. | $R^3$ | $R^4$ | $R^5$ | $Y^1$ | $Y^2$ | $Y^3$ | X | Z | $R^1$ | $R^2$ | Physical properties (m.p., refractive index, $^1H$-NMR ($CDCl_3$, δ)) |
|---|---|---|---|---|---|---|---|---|---|---|---|
| (73) | H | H | 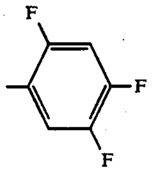 | H | H | H | O | CCl | $OCH_3$ | $OCH_3$ | |
| (74) | $CH_3$ | H | $CH_3$ | H | H | H | O | CH | $OCH_3$ | $OCH_3$ | $n_D^{21}$ 1.5002 |
| (75) | $CH_3$ | H | $CH_3$ | H | H | H | O | N | $OCH_3$ | $OCH_3$ | $n_D^{21}$ 1.4475 |
| (76) | H | | $(CH_2)_6$ | H | H | H | O | CH | $OCH_3$ | $OCH_3$ | m.p. 92–94° C. |
| (77) | H | | $(CH_2)_6$ | H | H | H | O | N | $OCH_3$ | $OCH_3$ | $n_D^{21}$ 1.5293 |
| (78) | H | | $(CH_2)_6$ | H | H | H | O | CF | $OCH_3$ | $OCH_3$ | |
| (79) | H | | $(CH_2)_6$ | H | H | H | O | CCl | $OCH_3$ | $OCH_3$ | |
| (80) | H | | $(CH_2)_6$ | H | H | H | S | CCl | $OCH_3$ | $OCH_3$ | |
| (81) | H | | $(CH_2)_6$ | H | H | H | O | CBr | $OCH_3$ | $OCH_3$ | |
| (82) | H | H | 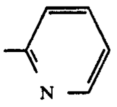 | H | H | H | O | CF | $OCH_3$ | $OCH_3$ | |
| (83) | H | H | 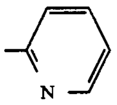 | H | H | H | O | CCl | $OCH_3$ | $OCH_3$ | |
| (84) | H | H | 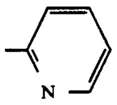 | H | H | H | O | CBr | $OCH_3$ | $OCH_3$ | |
| (85) | H | H | 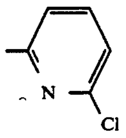 | H | H | H | O | $COCH_3$ | $OCH_3$ | $OCH_3$ | |
| (86) | H | H | 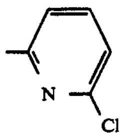 | H | H | H | O | $CCH_3$ | $OCH_3$ | $OCH_3$ | |
| (87) | H | H | 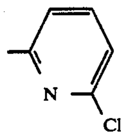 | H | H | H | O | CCl | $OCH_3$ | $OCH_3$ | |

TABLE 1-continued
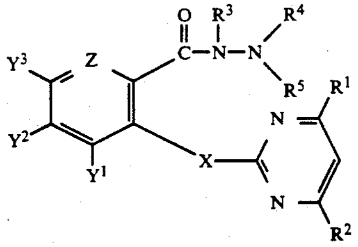
| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (88) | H | H | 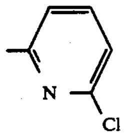 | H | H | H | O | CH | $OCH_3$ | $OCH_3$ | $n_D^{21}$ 1.5412 |
| (89) | H | H | 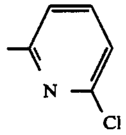 | H | H | H | O | N | $OCH_3$ | $OCH_3$ | $n_D^{21}$ 1.4968 |
| (90) | H | H | 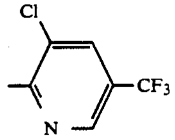 | H | H | H | O | CH | $OCH_3$ | $OCH_3$ | $n_D^{21}$ 1.4928 |
| (91) | H | H | 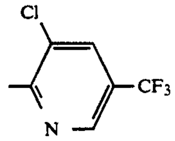 | H | H | H | O | N | $OCH_3$ | $OCH_3$ | $n_D^{21}$ 1.4832 |
| (92) | H | H | 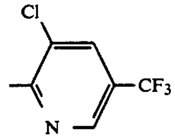 | H | H | H | O | CCl | $OCH_3$ | $OCH_3$ | |
| (93) | H | H | 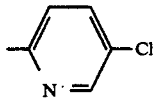 | H | H | H | O | CF | $OCH_3$ | $OCH_3$ | |
| (94) | H | H | 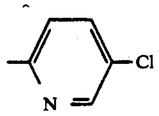 | H | H | H | O | CCl | $OCH_3$ | $OCH_3$ | |
| (95) | H | H | 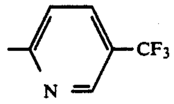 | H | H | H | O | CF | $OCH_3$ | $OCH_3$ | |
| (96) | H | H | 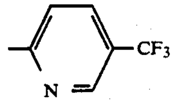 | H | H | H | S | CCl | $OCH_3$ | $OCH_3$ | |

TABLE 1-continued

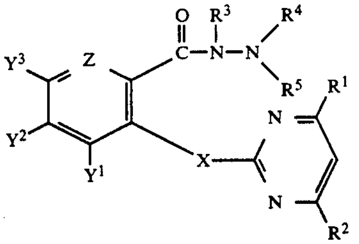

| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (97) | H | H | 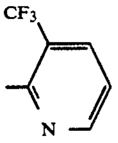 | H | H | H | O | CBr | $OCH_3$ | $OCH_3$ | |
| (98) | H | H | 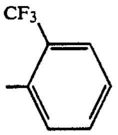 | H | H | H | O | CCl | $OCH_3$ | $OCH_3$ | |
| (99) | H | H | 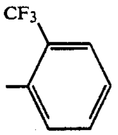 | H | H | H | O | CF | $OCH_3$ | $OCH_3$ | |
| (100) | H | H | 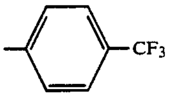 | H | H | H | O | CCl | $OCH_3$ | $OCH_3$ | |
| (101) | H | H | 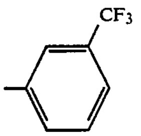 | H | H | H | O | CCl | $OCH_3$ | $OCH_3$ | |
| (102) | H | H | 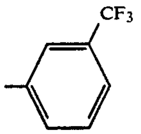 | H | H | H | O | CH | $OCH_3$ | $OCH_3$ | $n_D^{21}$ 1.4998 |
| (103) | H | H | 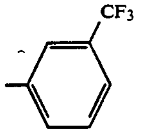 | H | H | H | O | N | $OCH_3$ | $OCH_3$ | $n_D^{21}$ 1.4697 |
| (104) | H | | $(CH_2)_4$ | H | H | H | O | CH | $OCH_3$ | $OCH_3$ | $n_D^{21}$ 1.5348 |
| (105) | H | | $(CH_2)_4$ | H | H | H | O | N | $OCH_3$ | $OCH_3$ | $n_D^{21}$ 1.5341 |
| (106) | H | | $(CH_2)_4$ | H | H | H | O | CF | $OCH_3$ | $OCH_3$ | |
| (107) | H | | $(CH_2)_4$ | H | H | H | O | CCl | $OCH_3$ | $OCH_3$ | |
| (108) | H | | $(CH_2)_4$ | H | H | H | O | CBr | $OCH_3$ | $OCH_3$ | |
| (109) | H | | $CH_3$ $CH_3$<br>$CH_2CH—O—CHCH_2$ | H | H | H | O | CF | $OCH_3$ | $OCH_3$ | |
| (110) | H | | $CH_3$ $CH_3$<br>$CH_2CH—O—CHCH_2$ | H | H | H | O | CCl | $OCH_3$ | $OCH_3$ | |

TABLE 1-continued

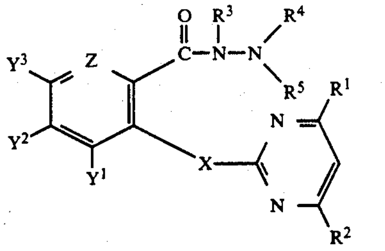

| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (111) | H | | $CH_3$ $CH_3$<br>$CH_2CH—O—CHCH_2$ | H | H | H | O | CBr | $OCH_3$ | $OCH_3$ | |
| (112) | H | | $(CH_2)_2—O—(CH_2)_2$ | H | H | H | O | CF | $OCH_3$ | $OCH_3$ | |
| (113) | H | | $(CH_2)_2—O—(CH_2)_2$ | H | H | H | O | CCl | $OCH_3$ | $OCH_3$ | |
| (114) | H | | $CH_3$ $CH_3$<br>$CH—(CH_2)_3—CH$ | H | H | H | O | CF | $OCH_3$ | $OCH_3$ | |
| (115) | H | | $CH_3$ $CH_3$<br>$CH—(CH_2)_3—CH$ | H | H | H | O | CCl | $OCH_3$ | $OCH_3$ | |
| (116) | H | | $CH_3$ $CH_3$<br>$CH—(CH_2)_3—CH$ | H | H | H | O | CH | $OCH_3$ | $OCH_3$ | $n_D^{21}$ 1.4992 |
| (117) | H | | $CH_3$ $CH_3$<br>$CH—(CH_2)_2—CH$ | H | H | H | O | N | $OCH_3$ | $OCH_3$ | $n_D^{21}$ 1.4805 |
| (118) | H | | $(CH_2)_2—O—(CH)_2$ | H | H | H | O | CH | $OCH_3$ | $OCH_3$ | $n_D^{21}$ 1.4981 |
| (119) | H | | $(CH_2)_2—O—(CH)_2$ | H | H | H | O | N | $OCH_3$ | $OCH_3$ | m.p. 161-162° C. |
| (120) | H | H | 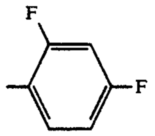 | H | H | H | O | CF | $OCH_3$ | $OCH_3$ | m.p. 141-143° C. |
| (121) | H | H | 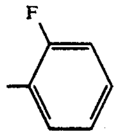 | H | H | H | O | CF | $OCH_3$ | $OCH_3$ | m.p. 58-59° C. |
| (122) | H | H | 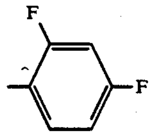 | H | H | H | O | CCl | $OCH_3$ | $OCH_3$ | m.p. 71-72° C. |
| (123) | H | H | 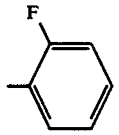 | H | H | H | O | CCl | $OCH_3$ | $OCH_3$ | m.p. 85-87° C. |
| (124) | H | H | 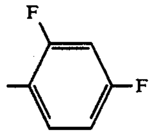 | H | H | H | O | CBr | $OCH_3$ | $OCH_3$ | |

TABLE 1-continued
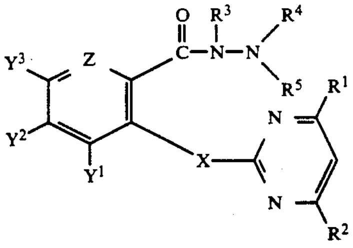
| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (125) | H | H | 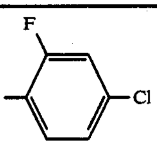 | H | H | H | O | CCl | $OCH_3$ | $OCH_3$ | |
| (126) | H | H | 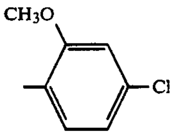 | H | H | H | O | CCl | $OCH_3$ | $OCH_3$ | |
| (127) | H | H | 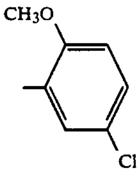 | H | H | H | O | CCl | $OCH_3$ | $OCH_3$ | |
| (128) | H | H | 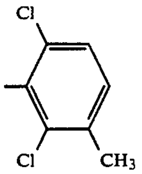 | H | H | H | O | CCl | $OCH_3$ | $OCH_3$ | |
| (129) | H | H | 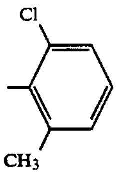 | H | H | H | O | CCl | $OCH_3$ | $OCH_3$ | |
| (130) | H | H | 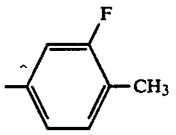 | H | H | H | O | CCl | $OCH_3$ | $OCH_3$ | |
| (131) | H | H | 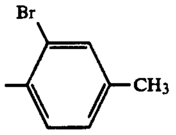 | H | H | H | O | CCl | $OCH_3$ | $OCH_3$ | |
| (132) | H | H | 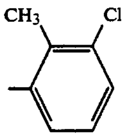 | H | H | H | O | CCl | $OCH_3$ | $OCH_3$ | |

TABLE 1-continued

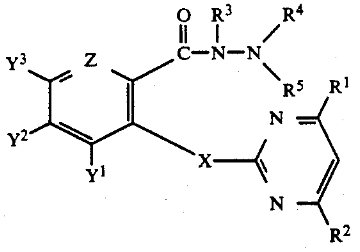

| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (133) | H | H | 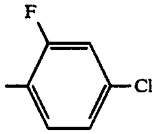 | H | H | H | O | CCl | $OCH_3$ | $OCH_3$ | |
| (134) | H | H | 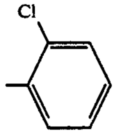 | H | H | H | O | CCl | $OCH_3$ | $OCH_3$ | m.p. 55-57° C. |
| (135) | H | H | 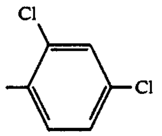 | H | H | H | O | CCl | $OCH_3$ | $OCH_3$ | glassy |
| (136) | H | | $(CH_2)_5$ | H | H | H | O | N | $OCH_3$ | $OCH_3$ | $n_D^{21}$ 1.4713 |
| (137) | H | $CH_3$ | 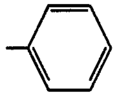 | H | H | H | O | CH | $OCH_3$ | $OCH_3$ | m.p. 151-152° C. |
| (138) | H | H | 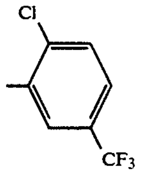 | H | H | H | O | CCl | $OCH_3$ | $OCH_3$ | |
| (139) | H | H | 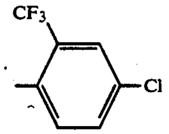 | H | H | H | O | CCl | $OCH_3$ | $OCH_3$ | |
| (140) | H | H | 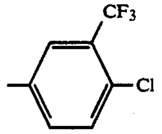 | H | H | H | O | CCl | $OCH_3$ | $OCH_3$ | |
| (141) | H | H | 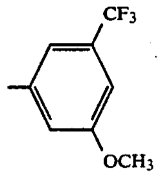 | H | H | H | O | CCl | $OCH_3$ | $OCH_3$ | |

TABLE 1-continued

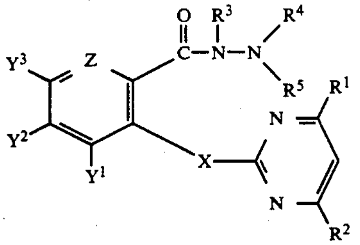

| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (142) | H | H | 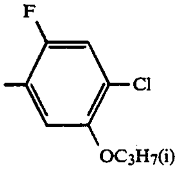 | H | H | H | O | CCl | $OCH_3$ | $OCH_3$ | |
| (143) | H | H | 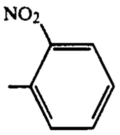 | H | H | H | O | CF | $OCH_3$ | $OCH_3$ | |
| (144) | H | H | 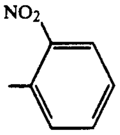 | H | H | H | O | CCl | $OCH_3$ | $OCH_3$ | |
| (145) | H | H | 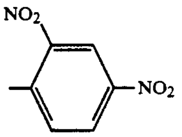 | H | H | H | O | CCl | $OCH_3$ | $OCH_3$ | |
| (146) | H | H | 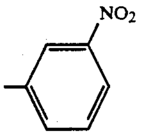 | H | H | H | O | CF | $OCH_3$ | $OCH_3$ | |
| (147) | H | H | 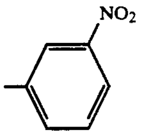 | H | H | H | O | CCl | $OCH_3$ | $OCH_3$ | |
| (148) | H | $CH_3$ | $CH_3$ | H | Cl | H | O | CH | $OCH_3$ | $OCH_3$ | glassy |
| (149) | H | $CH_3$ | $CH_3$ | H | $CH_3$ | H | O | CH | $OCH_3$ | $OCH_3$ | glassy |
| (150) | $CH_3$ | H | H | H | H | H | O | CH | $OCH_3$ | $OCH_3$ | mixture |
| | H | H | $CH_3$ | | | | | | | | ($n_D^{24}$ 1.5562) |
| (151) | H | H | 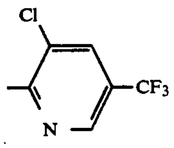 | H | H | H | O | CCl | $OCH_3$ | $OCH_3$ | $n_D^{19}$ 1.5523 |
| (152) | $C_6H_5$ | $C_6H_5$ | H | H | H | H | O | CCl | $OCH_3$ | $OCH_3$ | |
| (153) | $C_6H_5$ | $C_6H_5$ | H | H | H | H | S | CCl | $OCH_3$ | $OCH_3$ | |
| (154) | H | $C_6H_5$ | $C_6H_5$ | H | H | H | O | CF | $OCH_3$ | $OCH_3$ | |
| (155) | H | $C_6H_5$ | $C_6H_5$ | H | H | H | O | CCl | $OCH_3$ | $OCH_3$ | |
| (156) | H | $C_6H_5$ | $C_6H_5$ | H | H | H | O | CBr | $OCH_3$ | $OCH_3$ | |

TABLE 1-continued

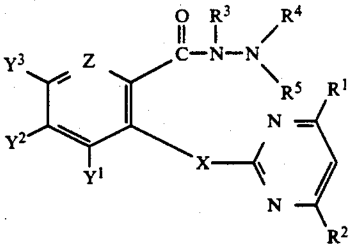

| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (157) | H | H | 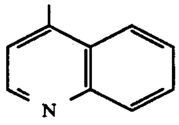 | H | H | H | O | CCl | $OCH_3$ | $OCH_3$ | |
| (158) | H | H | 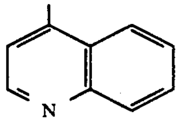 | H | H | H | O | N | $OCH_3$ | $OCH_3$ | |
| (159) | H | H | 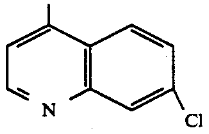 | H | H | H | O | CH | $OCH_3$ | $OCH_3$ | |
| (160) | H | H | 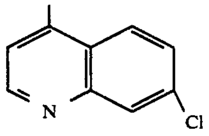 | H | H | H | O | N | $OCH_3$ | $OCH_3$ | |
| (161) | H | H | 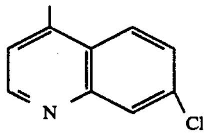 | H | H | H | O | CF | $OCH_3$ | $OCH_3$ | |
| (162) | H | $CH_3$ | 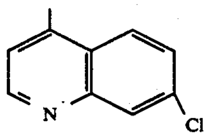 | H | H | H | O | CCl | $OCH_3$ | $OCH_3$ | glassy |
| (163) | H | H | 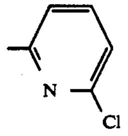 | H | H | H | O | CCl | $OCH_3$ | $OCH_3$ | glassy |
| (164) | H | H | 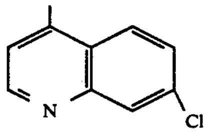 | H | H | H | O | CCl | $OCH_3$ | $OCH_3$ | m.p. 183–184° C. |
| (165) | H | $CH_3$ | $CH_3$ | H | H | H | O | CF | $OCH_3$ | $OCH_3$ | $n_D^{19}$ 1.5257 |
| (166) | H | H | $COCH_3$ | H | H | H | O | CH | $OCH_3$ | $OCH_3$ | glassy |
| (167) | H | H | $COOCH_3$ | H | H | H | O | CH | $OCH_3$ | $OCH_3$ | $n_D^{21}$ 1.5338 |

TABLE 1-continued

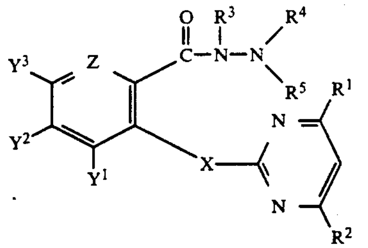

| Compound No. | $R^3$ | $R^4$ | $R^5$ | $Y^1$ | $Y^2$ | $Y^3$ | X | Z | $R^1$ | $R^2$ | Physical properties (m.p., refractive index, $^1$H-NMR ($CDCl_3$, δ)) |
|---|---|---|---|---|---|---|---|---|---|---|---|
| (168) | H | H | $COOCH_3$ | H | H | H | O | N | $OCH_3$ | $OCH_3$ | $n_D^{21}$ 1.5351 |
| (169) | H | | $COOCH_2CH_2$ | H | H | H | O | CF | $OCH_3$ | $OCH_3$ | $n_D^{19}$ 1.5472 |
| (170) | H | | $COOCH_2CH_2$ | H | H | H | O | N | $OCH_3$ | $OCH_3$ | $n_D^{19}$ 1.5281 |
| (171) | H | | $COOCH_2CH_2$ | H | H | H | O | CH | $OCH_3$ | $OCH_3$ | $n_D^{19}$ 1.5730 |
| (172) | H | | $COOCH_2CH_2$ | H | H | H | O | CCl | $OCH_3$ | $OCH_3$ | glassy |
| (173) | H | H | $COCH_3$ | H | H | H | O | CCl | $OCH_3$ | $OCH_3$ | |
| (174) | H | H | $COCH_2CH_3$ | H | H | H | O | CCl | $OCH_3$ | $OCH_3$ | |
| (175) | H | H | $COC_6H_{13}(n)$ | H | H | H | O | CCl | $OCH_3$ | $OCH_3$ | |
| (176) | H | H | $COOCH_3$ | H | H | H | O | CCl | $OCH_3$ | $OCH_3$ | |
| (177) | H | H | $COOCH_2CH_3$ | H | H | H | O | CCl | $OCH_3$ | $OCH_3$ | |
| (178) | H | H | $COOC_6H_{13}(n)$ | H | H | H | O | CCl | $OCH_3$ | $OCH_3$ | |
| (179) | H | | $COCH_2CH_2CH_2$ | H | H | H | O | CCl | $OCH_3$ | $OCH_3$ | |
| (180) | H | | $COCH_2CH_2CH_2CH_2$ | H | H | H | O | CCl | $OCH_3$ | $OCH_3$ | |
| (181) | H | | $COOCH_2CH_2CH_2$ | H | H | H | O | CF | $OCH_3$ | $OCH_3$ | |
| (182) | H | | $COOCH_2CH_2CH_2$ | H | H | H | O | CCl | $OCH_3$ | $OCH_3$ | |
| (183) | H | | 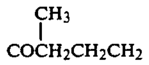 | H | H | H | O | CCl | $OCH_3$ | $OCH_3$ | |
| (184) | H | | 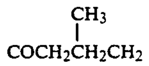 | H | H | H | O | CCl | $OCH_3$ | $OCH_3$ | |
| (185) | H | | 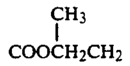 | H | H | H | O | CCl | $OCH_3$ | $OCH_3$ | |
| (186) | H | | 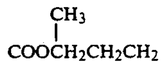 | H | H | H | O | CF | $OCH_3$ | $OCH_3$ | |
| (187) | H | | 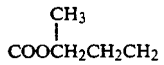 | H | H | H | O | CCl | $OCH_3$ | $OCH_3$ | |
| (188) | H | | 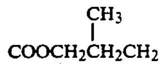 | H | H | H | O | CCl | $OCH_3$ | $OCH_3$ | |
| (189) | H | $CH_3$ | $CH_3$ | H | H | H | O | 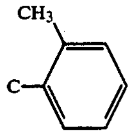 | $OCH_3$ | $OCH_3$ | |
| (190) | H | $CH_3$ | $CH_3$ | H | H | H | O | 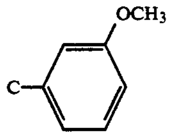 | $OCH_3$ | $OCH_3$ | |
| (191) | H | $CH_3$ | $CH_3$ | H | H | H | O | 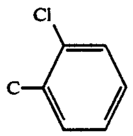 | $OCH_3$ | $OCH_3$ | |

TABLE 1-continued

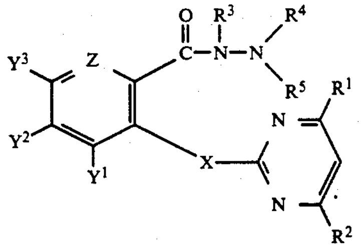

| Compound No. | $R^3$ | $R^4$ | $R^5$ | $Y^1$ | $Y^2$ | $Y^3$ | X | Z | $R^1$ | $R^2$ | Physical properties (m.p., refractive index, $^1H$-NMR ($CDCl_3$, δ)) |
|---|---|---|---|---|---|---|---|---|---|---|---|
| (192) | H | $CH_3$ | $CH_3$ | H | H | H | O | 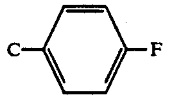 | $OCH_3$ | $OCH_3$ | |
| (193) | H | $CH_3$ | $CH_3$ | H | H | H | O | 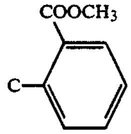 | $OCH_3$ | $OCH_3$ | |
| (194) | H | $CH_3$ | $CH_3$ | H | H | H | O | 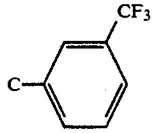 | $OCH_3$ | $OCH_3$ | |
| (195) | H | $CH_3$ | $CH_3$ | H | H | H | O | 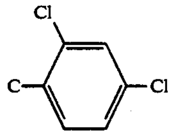 | $OCH_3$ | $OCH_3$ | |
| (196) | H | $CH_3$ | $CH_3$ | H | H | H | O | 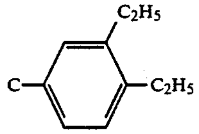 | $OCH_3$ | $OCH_3$ | |
| (197) | H | | $COOCH_2CH_2$ | H | H | H | O | $CCF_3$ | $OCH_3$ | $OCH_3$ | |
| (198) | H | | $COOCH_2CH_2$ | H | H | H | O | $CCH_3$ | $OCH_3$ | $OCH_3$ | |
| (199) | H | | $COOCH_2CH_2$ | H | H | H | O | $COCH_3$ | $OCH_3$ | $OCH_3$ | |
| (200) | H | | $COOCH_2CH_2$ | H | H | H | O | $CC_6H_5$ | $OCH_3$ | $OCH_3$ | |
| (201) | H | | $COOCH_2CH_2$ | H | H | H | O | CBr | $OCH_3$ | $OCH_3$ | |
| (202) | H | | $COOCH_2CH_2$ | H | H | H | S | CCl | $OCH_3$ | $OCH_3$ | |
| (203) | H | | $COCH_2CH_2CH_2$ | H | H | H | S | CCl | $OCH_3$ | $OCH_3$ | |
| (204) | H | H | 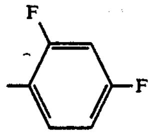 | H | H | H | S | CCl | $OCH_3$ | $OCH_3$ | |

Formulation Examples are shown below. In the examples, the present compound (I) is shown by Compound No. in Table 1, and parts are by weight.

FORMULATION EXAMPLE 1

Fifty parts of any one of the present compounds (1), (3), (15), (16), (28), (31), (43), (59), (60), (61), (76), (119), (120), (121), (122), (123), (134) and (164), 3 parts of calcium lignosulfonate, 2 parts of sodium lauryl sulfate and 45 parts of synthetic hydrated silicon dioxide are well mixed to obtain a wettable powder.

FORMULATION EXAMPLE 2

Two parts of any one of the present compounds (1) to (3), (14) to (17), (28) to (31), (42) to (45), (56) to (63), (74) to (77), (88) to (91), (102) to (105), (116) to (123), (134) to (137), (148) to (151), (162) to (171) and (172), 9 parts of Toxanone P-8L (mfd. by SANYO CHEMICAL INDUSTRIES, INC.) and 89 parts of cyclohexanone are well mixed to obtain an emulsifiable concentrate.

FORMULATION EXAMPLE 3

Two parts of any one of the present compounds (1) to (3), (14) to (17), (28) to (31), (42) to (45), (56) to (63), (74) to (77), (88) to (91), (102) to (105), (116) to (123), (134) to (137), (148) to (151), (162) to (171) and (172}, 1 part of synthetic hydrated silicon, 2 parts of calcium lignosulfonate, 30 parts of bentonite and 65 parts of kaolin clay are well pulverized and mixed. The resulting mixture is well kneaded with water, granulated and dried to obtain a granule.

FORMULATION EXAMPLE 4

Twenty five parts of any one of the present compounds (1) to (3), (14) to (17), (28) to (31), (42) to (45), (56) to (63), (74) to (77), (88) to (91), (102) to (105), (116) to (123), (134) to (137), (148) to (151), (162) to (171) and (172), 3 parts of polyoxyethylene sorbitan monooleate, 3 parts of CMC and 69 parts of water are mixed and wet-pulverized until the particle size decreases to 5 microns or less. Thus, a suspension formulation is obtained.

That the present compounds are useful as an active ingredient for herbicides is shown by the following test examples. In the examples, the present compound (I) is shown by Compound No. in Table 1, and compounds used for comparison are shown by Compound symbol in Table 2.

TABLE 2

| Compound symbol | Structural formula | Remarks |
|---|---|---|
| A | 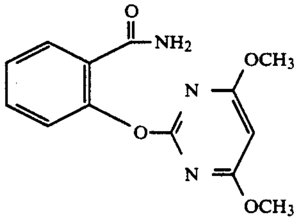 | Comparative Compound (mp: 138-139° C.) |
| B | 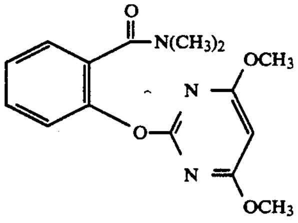 | Comparative Compound ($n_D^{23}$ 1.5475) |
| C | 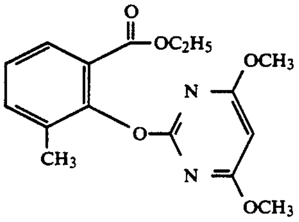 | EP-0 249 708-Al ($n_D^{23}$ 1.5271) |

TABLE 2-continued

| Compound symbol | Structural formula | Remarks |
|---|---|---|
| D | 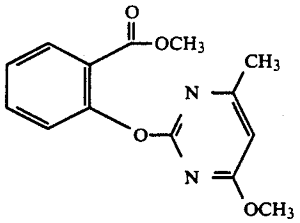 | EP-0 223 406-Al (Compound No. 16) |
| E | 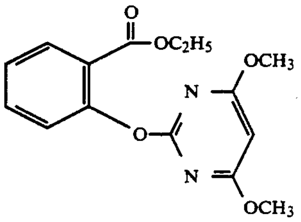 | EP-0 223 406-Al (Compound No. 18) |
| F | 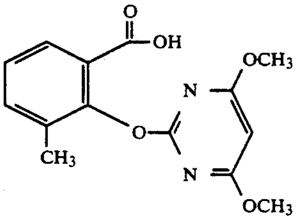 | EP-0 249 708-Al (Compound No. 1) |
| G | 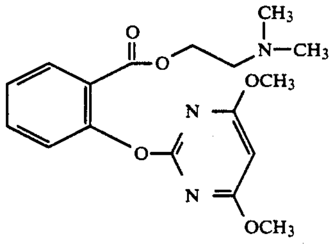 | Comparative Compound ($n_D^{19}$ 1.5298) |
| H | 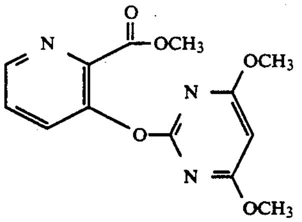 | EP-0 249 707-Al (Compound No. 1) |

The determination of the herbicidal activity and phytotoxicity was carried out as follows: When the states of emergence and growth of treated test plants (weeds and crops) at the time of determination were completely the same as or hardly different from those of untreated test plants, the value of determination was taken as "0". When the treated test plants were completely killed, or their emergence and growth were completely inhibited, the value of determination was taken as "5", and an interval between "0" and "5" was divided into four stages, i.e. "1", "2", "3" and "4". The evaluation was thus made in six stages.

TEST EXAMPLE 1 SOIL SURFACE TREATMENT TEST IN UPLAND FIELD SOIL

Cylindrical plastic pots of 10 cm in diameter and 10 cm in depth were filled with upland field soil, and seeds of Japanese millet, oat and velvetleaf were sowed in the respective pots and covered with soil. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 19 days in a greenhouse, and the herbicidal activity was examined. The results are shown in the table below.

| Test compound | Dosage rate of active ingredient (g/a) | Herbicidal activity Japanese millet | Oat | Velvetleaf |
|---|---|---|---|---|
| (1) | 5 | 5 | 4 | 4 |
| (3) | 5 | 5 | 5 | 4 |
| (14) | 5 | 5 | 4 | 4 |
| (15) | 5 | 5 | 5 | 4 |
| (16) | 5 | 5 | 4 | 5 |
| (17) | 5 | 4 | 4 | 4 |
| (28) | 5 | 5 | 4 | 4 |
| (29) | 5 | 3 | 4 | 4 |
| (30) | 5 | 3 | 3 | 4 |
| (31) | 5 | 5 | 4 | 4 |
| (42) | 5 | 5 | 4 | 4 |
| (43) | 5 | 5 | 5 | 4 |
| (44) | 5 | 5 | 4 | 4 |
| (45) | 5 | 5 | 4 | 4 |
| (56) | 5 | 5 | 4 | 4 |
| (57) | 5 | 5 | 5 | 4 |
| (58) | 5 | 5 | 5 | 4 |
| (59) | 5 | 5 | 5 | 5 |
| (61) | 5 | 5 | 5 | 4 |
| (62) | 5 | 5 | 4 | 5 |
| (63) | 5 | 5 | 5 | 5 |
| (74) | 5 | 5 | 4 | 5 |
| (76) | 5 | 5 | 4 | 4 |
| (88) | 5 | 5 | 4 | 4 |
| (90) | 5 | 5 | 5 | 4 |
| (102) | 5 | 5 | 4 | 4 |
| (105) | 5 | 5 | 4 | 4 |
| (118) | 5 | 5 | 4 | 4 |
| (120) | 5 | 5 | 5 | 4 |
| (121) | 5 | 5 | 5 | 4 |
| (122) | 5 | 5 | 5 | 4 |
| (123) | 5 | 5 | 4 | 4 |
| (134) | 5 | 5 | 4 | 4 |
| (135) | 5 | 5 | 4 | 4 |
| (150) | 5 | 5 | 4 | 4 |
| (162) | 5 | 5 | 3 | 4 |
| (165) | 5 | 5 | 5 | 4 |
| (169) | 5 | 5 | 5 | 5 |
| (171) | 5 | 5 | 4 | 4 |
| (172) | 5 | 5 | 5 | 5 |
| A | 5 | 0 | 0 | 1 |
| B | 5 | 0 | 0 | 0 |

TEST EXAMPLE 2 SOIL SURFACE TREATMENT TEST IN UPLAND FIELD SOIL

Cylindrical plastic pots of 10 cm in diameter and 10 cm in depth were filled with upland field soil, and seeds of tall morningglory were sowed in the respective pots and covered with soil. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 19 days in a greenhouse, and the herbicidal activity was examined. The results are shown in the table below.

| Test compound | Dosage rate of active ingredient (g/a) | Herbicidal activity Tall morningglory |
|---|---|---|
| (62) | 5 | 4 |
| (63) | 5 | 4 |
| (76) | 5 | 4 |
| (120) | 5 | 4 |
| (121) | 5 | 4 |
| (122) | 5 | 4 |
| (135) | 5 | 4 |
| (172) | 5 | 4 |
| A | 5 | 2 |
| B | 5 | 0 |
| C | 5 | 0 |
| D | 5 | 0 |
| F | 5 | 0 |
| G | 5 | 0 |

TEST EXAMPLE 3 SOIL SURFACE TREATMENT TEST IN UPLAND FIELD SOIL

Cylindrical plastic pots of 10 cm in diameter and 10 cm in depth were filled with upland field soil, and seeds of Japanese millet were sowed in the respective pots and covered with soil. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 19 days in a greenhouse, and the herbicidal activity was examined. The results are shown in the table below.

| Test compound | Dosage rate of active ingredient (g/a) | Herbicidal activity Japanese millet |
|---|---|---|
| (77) | 5 | 5 |
| A | 5 | 0 |
| B | 5 | 0 |

TEST EXAMPLE 4 FOLIAR TREATMENT TEST IN UPLAND FIELD SOIL

Cylindrical plastic pots of 10 cm in diameter and 10 cm in depth were filled with upland field soil, and seeds of Japanese millet, oat, radish, velvetleaf and tall morningglory were sowed in the respective pots and cultivated for 8 days in a greenhouse.

Thereafter, the test compounds were formulated into emulsifiable concentrates according to Formulation Example 2, and the prescribed amount of each emulsifiable concentrate was diluted with a spreading agent-containing water corresponding to 10 liters/are and uniformly applied from above onto the whole foliar portion of the test plants by means of an automatic sprayer. After application, the test plants were cultivated for 19 days in a greenhouse, and the herbicidal activity was examined.

The results are shown in the table below.

| Test compound | Dosage rate of active ingredient (g/a) | Herbicidal activity | | | | |
|---|---|---|---|---|---|---|
| | | Japanese millet | Oat | Radish | Velvet leaf | Tall morning-glory |
| (1) | 5 | 5 | 4 | 4 | 4 | 3 |
| (3) | 5 | 5 | 4 | 3 | 4 | 4 |
| (14) | 5 | 5 | 4 | 4 | 4 | 4 |
| (15) | 5 | 5 | 4 | 4 | 5 | 4 |
| (16) | 5 | 5 | 4 | 4 | 4 | 4 |
| (28) | 5 | 4 | 3 | 3 | 4 | 4 |
| (29) | 5 | 5 | 5 | 5 | 5 | 4 |
| (30) | 5 | 5 | 5 | 5 | 5 | 5 |
| (31) | 5 | 4 | 4 | 3 | 3 | 3 |
| (42) | 5 | 5 | 4 | 3 | 3 | 4 |
| (43) | 5 | 4 | 4 | 4 | 4 | 3 |
| (44) | 5 | 5 | 5 | 4 | 4 | 4 |
| (45) | 5 | 5 | 4 | 4 | 4 | 4 |
| (56) | 5 | 5 | 4 | 4 | 4 | 5 |
| (57) | 5 | 5 | 4 | 4 | 4 | 3 |
| (58) | 5 | 5 | 4 | 4 | 4 | 4 |
| (59) | 5 | 5 | 5 | 4 | 4 | 4 |
| (60) | 5 | 4 | 4 | 4 | 4 | 3 |
| (62) | 5 | 5 | 5 | 5 | 5 | 4 |
| (63) | 5 | 5 | 4 | 5 | 5 | 5 |
| (74) | 5 | 5 | 4 | 3 | 4 | 4 |
| (77) | 5 | 5 | 4 | 4 | 5 | 4 |
| (102) | 5 | 5 | 4 | 4 | 4 | 4 |
| (104) | 5 | 5 | 4 | 4 | 4 | 4 |
| (105) | 5 | 5 | 4 | 4 | 4 | 4 |
| (118) | 5 | 5 | 4 | 4 | 4 | 4 |
| (119) | 5 | 5 | 4 | 4 | 5 | 4 |
| (120) | 5 | 4 | 5 | 5 | 5 | 5 |
| (121) | 5 | 4 | 5 | 5 | 5 | 5 |
| (122) | 5 | 5 | 4 | 5 | 5 | 5 |
| (123) | 5 | 5 | 3 | 5 | 5 | 5 |
| (134) | 5 | 5 | 3 | 5 | 4 | 5 |
| (135) | 5 | 5 | 3 | 5 | 5 | 5 |
| (136) | 5 | 4 | 4 | 4 | 5 | 4 |
| (150) | 5 | 4 | 4 | 4 | 5 | 3 |
| (162) | 5 | 5 | 4 | 5 | 5 | 5 |
| (163) | 5 | 4 | 3 | 5 | 4 | 5 |
| (165) | 5 | 4 | 5 | 4 | 5 | 4 |
| (169) | 5 | 5 | 5 | 5 | 5 | 5 |
| (172) | 5 | 5 | 5 | 5 | 5 | 5 |
| A | 5 | 1 | 0 | 0 | 0 | 3 |
| B | 5 | 0 | 0 | 0 | 0 | 0 |
| D | 5 | 3 | 2 | 2 | 1 | 3 |
| F | 5 | 3 | 3 | 1 | 1 | 1 |

TEST EXAMPLE 5 FOLIAR TREATMENT TEST IN UPLAND FIELD SOIL

Cylindrical plastic pots of 10 cm in diameter and 10 cm in depth were filled with upland field soil, and seeds of radish were sowed in the respective pots and cultivated for 8 days in a greenhouse.

Thereafter, the test compounds were formulated into emulsifiable concentrates according to Formulation Example 2, and the prescribed amount of each emulsifiable concentrate was diluted with a spreading agent-containing water corresponding to 10 liters/are and uniformly applied from above onto the whole foliar portion of the test plants by means of an automatic sprayer. After application, the test plants were cultivated for 19 days in a greenhouse, and the herbicidal activity was examined.

The results are shown in the table below.

| Test compound | Dosage rate of active ingredient (g/a) | Herbicidal activity Radish |
|---|---|---|
| (164) | 5 | 5 |
| C | 5 | 1 |

-continued

| Test compound | Dosage rate of active ingredient (g/a) | Herbicidal activity Radish |
|---|---|---|
| G | 5 | 3 |

TEST EXAMPLE 6 FLOODING TREATMENT TEST IN PADDY FIELD

Cylindrical plastic pots of 8 cm in diameter and 12 cm in depth were filled with paddy field soil, and seeds of barnyardgrass and bulrush were sowed 1 to 2 cm deep under the soil surface. After creating the state of paddy field by flooding, a tuber of arrowhead was buried 1 to 2 cm deep under the soil surface and cultivated in a greenhouse. After 6 days (at the initial stage of generation of every weed), the test compounds were formulated into emulsifiable concentrates according to Formulation Example 2, and the prescribed amount of each emulsifiable concentrate was diluted with 2.5 ml of water and applied onto the water surface. After application, the test plants were cultivated for 19 days in a greenhouse, and the herbicidal activity was examined. The results are shown in the table below.

| Test compound | Dosage rate of active ingredient (g/a) | Herbicidal activity | | |
|---|---|---|---|---|
| | | Barnyard-grass | Bulrush | Arrow-head |
| (1) | 2.5 | 4 | 4 | 4 |
| (3) | 2.5 | 4 | 5 | 4 |
| (14) | 2.5 | 4 | 4 | 4 |
| (15) | 2.5 | 4 | 4 | 4 |
| (16) | 2.5 | 5 | 5 | 5 |
| (17) | 2.5 | 4 | 3 | 3 |
| (29) | 2.5 | 4 | 3 | 3 |
| (30) | 2.5 | 4 | 4 | 4 |
| (42) | 2.5 | 4 | 4 | 3 |
| (43) | 2.5 | 4 | 5 | 4 |
| (45) | 2.5 | 4 | 4 | 3 |
| (56) | 2.5 | 4 | 4 | 4 |
| (57) | 2.5 | 4 | 4 | 4 |
| (58) | 2.5 | 4 | 4 | 4 |
| (59) | 2.5 | 4 | 5 | 4 |
| (61) | 2.5 | 5 | 5 | 4 |
| (62) | 2.5 | 5 | 5 | 4 |
| (63) | 2.5 | 5 | 5 | 5 |
| (74) | 2.5 | 5 | 5 | 4 |
| (76) | 2.5 | 5 | 5 | 5 |
| (77) | 2.5 | 5 | 4 | 3 |
| (88) | 2.5 | 5 | 5 | 4 |
| (90) | 2.5 | 5 | 5 | 4 |
| (104) | 2.5 | 5 | 5 | 4 |
| (105) | 2.5 | 5 | 5 | 4 |
| (119) | 2.5 | 5 | 5 | 3 |
| (121) | 2.5 | 4 | 4 | 5 |
| (122) | 2.5 | 5 | 4 | 4 |
| (134) | 2.5 | 4 | 5 | 4 |
| (135) | 2.5 | 3 | 5 | 4 |
| (136) | 2.5 | 5 | 5 | 4 |
| (162) | 2.5 | 5 | 5 | 5 |
| (163) | 2.5 | 5 | 4 | 5 |
| (165) | 2.5 | 5 | 5 | 5 |
| (167) | 2.5 | 5 | 4 | 4 |
| (169) | 2.5 | 5 | 5 | 5 |
| (171) | 2.5 | 5 | 5 | 5 |
| (172) | 2.5 | 5 | 5 | 5 |
| A | 2.5 | 0 | 0 | 0 |
| B | 2.5 | 3 | 0 | 0 |

TEST EXAMPLE 7 FLOODING TREATMENT TEST IN PADDY FIELD

Cylindrical plastic pots of 8 cm in diameter and 12 cm in depth were filled with paddy field soil, and seeds of barnyardgrass were sowed 1 to 2 cm deep under the soil surface. After creating the state of paddy field by flooding, rice plants of 2-leaf stage were transplanted therein and cultivated in a greenhouse. After 6 days (at the initial stage of generation of every weed), the test compounds were formulated into emulsifiable concentrates according to Formulation Example 2, and the prescribed amount of each emulsifiable concentrate was diluted with 2.5 ml of water and applied onto the water surface. After application, the test plants were cultivated for 19 days in a greenhouse, and the herbicidal activity and phytotoxicity were examined. The results are shown in the table below.

| Test compound | Dosage rate of active ingredient (g/a) | Phytotoxicity Rice | Herbicidal activity Barnyardgrass |
|---|---|---|---|
| (76) | 0.16 | 0 | 4 |
| (102) | 0.16 | 0 | 4 |
| (104) | 0.63 | 0 | 4 |
| (105) | 0.16 | 0 | 4 |
| (136) | 0.63 | 0 | 4 |
| F | 0.63 | 2 | 2 |
| G | 0.16 | 2 | 2 |
| H | 0.63 | 2 | 2 |

TEST EXAMPLE 8 FLOODING TREATMENT TEST IN PADDY FIELD

Cylindrical plastic pots of 8 cm in diameter and 12 cm in depth were filled with paddy field soil, and seeds of bulrush were sowed 1 to 2 cm deep under the soil surface. After creating the state of paddy field by flooding, rice plants of 2-leaf stage were transplanted therein and cultivated in a greenhouse. After 6 days (at the initial stage of generation of every weed), the test compounds were formulated into emulsifiable concentrates according to Formulation Example 2, and the prescribed amount of each emulsifiable concentrate was diluted with 2.5 ml of water and applied onto the water surface. After application, the test plants were cultivated for 19 days in a greenhouse, and the herbicidal activity and phytotoxicity were examined. The results are shown in the table below.

| Test compound | Dosage rate of active ingredient (g/a) | Phytotoxicity Rice | Herbicidal activity Bulrush |
|---|---|---|---|
| (61) | 0.16 | 0 | 4 |
| (76) | 0.16 | 0 | 4 |
| (102) | 0.16 | 0 | 4 |
| C | 2.5 | 3 | 1 |

-continued

| Test compound | Dosage rate of active ingredient (g/a) | Phytotoxicity Rice | Herbicidal activity Bulrush |
|---|---|---|---|
| D | 2.5 | 1 | 1 |

TEST EXAMPLE 9 FLOODING TREATMENT TEST IN PADDY FIELD

Cylindrical plastic pots of 8 cm in diameter and 12 cm in depth were filled with paddy field soil. After creating the state of paddy field by flooding, a tuber of arrowhead was buried 1 to 2 cm deep under the soil surface, rice plants of 2-leaf stage were transplanted therein and cultivated in a greenhouse. After 6 days (at the initial stage of generation of every weed), the test compounds were formulated into emulsifiable concentrates according to Formulation Example 2, and the prescribed amount of each emulsifiable concentrate was diluted with 2.5 ml of water and applied onto the water surface. After application, the test plants were cultivated for 19 days in a greenhouse, and the herbicidal activity and phytotoxicity were examined. The results are shown in the table below.

| Test compound | Dosage rate of active ingredient (g/a) | Phytotoxicity Rice | Herbicidal activity Arrowhead |
|---|---|---|---|
| (134) | 0.63 | 0 | 4 |
| (135) | 0.16 | 0 | 4 |
| (162) | 0.16 | 0 | 5 |
| (163) | 0.16 | 0 | 5 |
| (165) | 0.16 | 1 | 4 |
| F | 0.63 | 2 | 3 |
| H | 0.63 | 2 | 2 |

TEST EXAMPLE 10 SOIL TREATMENT TEST IN UPLAND FIELD SOIL

Vats of 33×23 cm2 in area and 11 cm in depth were filled with upland field soil, and seeds of soybean, velvetleaf, black nightshade, barnyardgrass, johnsongrass and giant foxtail were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 18 days in a greenhouse, and the herbicidal activity and phytotoxicity was examined. The results are shown in the table below.

| Test compound | Dosage rate of active ingredient (g/a) | Phytotoxicity Soybean | Herbicidal activity Velvet-leaf | Black nightshade | Barnyard-grass | Johnson-grass | Giant foxtail |
|---|---|---|---|---|---|---|---|
| (1) | 10 | 1 | 4 | 4 | 5 | 4 | 5 |
| | 2.5 | 0 | 3 | 4 | 4 | 4 | 4 |
| (3) | 10 | 1 | 4 | 4 | 5 | 5 | 5 |
| | 2.5 | 1 | 4 | 4 | 5 | 4 | 4 |
| (16) | 10 | 0 | 5 | 5 | 5 | 5 | 5 |
| | 2.5 | 0 | 4 | 5 | 5 | 4 | 4 |
| (28) | 10 | 1 | 4 | 5 | 5 | 5 | 5 |
| | 2.5 | 0 | 3 | 4 | 4 | 4 | 4 |
| (31) | 10 | 0 | 4 | 5 | 5 | 4 | 4 |
| (42) | 10 | 1 | 4 | 4 | 5 | 5 | 4 |
| (43) | 10 | 1 | 5 | 5 | 5 | 5 | 5 |
| | 2.5 | 1 | 4 | 5 | 5 | 4 | 5 |

-continued

| Test compound | Dosage rate of active ingredient (g/a) | Phytotoxicity Soybean | Herbicidal activity Velvet-leaf | Black nightshade | Barnyard-grass | Johnson-grass | Giant foxtail |
|---|---|---|---|---|---|---|---|
| (44) | 10 | 1 | 5 | 5 | 5 | 4 | 5 |
| | 2.5 | 1 | 4 | 4 | 5 | 4 | 4 |
| (45) | 10 | 1 | 5 | 5 | 5 | 5 | 4 |
| | 2.5 | 0 | 4 | 5 | 4 | 4 | 4 |
| (56) | 10 | 1 | 5 | 5 | 5 | 5 | 5 |
| | 2.5 | 1 | 4 | 5 | 5 | 4 | 4 |
| (58) | 10 | 1 | 5 | 5 | 5 | 5 | 5 |
| | 2.5 | 1 | 4 | 5 | 5 | 4 | 5 |
| (74) | 5 | 1 | 4 | 4 | 4 | 4 | 4 |
| (105) | 5 | 1 | 4 | 4 | 5 | 4 | 5 |
| C | 10 | 3 | 0 | 3 | 3 | 3 | 1 |
| | 2.5 | 2 | 0 | 2 | 1 | 2 | 0 |
| D | 10 | 2 | 0 | 3 | 2 | 2 | 2 |
| | 2.5 | 0 | 0 | 2 | 0 | 0 | 1 |
| E | 10 | 4 | 4 | 4 | 4 | 4 | 4 |
| | 2.5 | 3 | 3 | 4 | 3 | 4 | 4 |

TEST EXAMPLE 11 SOIL TREATMENT TEST IN UPLAND FIELD SOIL

Vats of 33×23 cm2 in area and 11 cm in depth were filled with upland field soil, and seeds of soybean, velvetleaf and sicklepod were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 18 days in a greenhouse, and the herbicidal activity and phytotoxicity were examined. The results are shown in the table below.

| Test compound | Dosage rate of active ingredient (g/a) | Phyto-toxicity Soybean | Herbicidal activity Velvet-leaf | Sicklepod |
|---|---|---|---|---|
| (76) | 2.5 | 0 | 4 | 4 |
| (105) | 1.25 | 0 | 4 | 4 |
| E | 2.5 | 3 | 3 | 0 |
| G | 5 | 1 | 1 | 2 |

TEST EXAMPLE 12 SOIL TREATMENT TEST IN UPLAND FIELD SOIL

Vats of 33×23 cm$^2$ in area and 11 cm in depth were filled with upland field soil, and seeds of cotton and barnyardgrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 18 days in a greenhouse, and the herbicidal activity and phytotoxicity were examined. The results are shown in the table below.

| Test compound | Dosage rate of active ingredient (g/a) | Phyto-toxicity Cotton | Herbicidal activity Barnyardgrass |
|---|---|---|---|
| (122) | 0.31 | 0 | 4 |
| C | 0.31 | 1 | 0 |
| D | 1.25 | 0 | 0 |
| E | 0.31 | 1 | 2 |
| F | 0.31 | 0 | 0 |
| H | 0.31 | 0 | 0 |

TEST EXAMPLE 13 FOLIAR TREATMENT TEST IN UPLAND FIELD SOIL

Vats of 33×23 cm$^2$ in area and 11 cm in depth were filled with upland field soil, and seeds of soybean, cotton, corn, rice, velvetleaf, black nightshade, barnyardgrass and johnsongrass were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds and crops at that time varied with the kind of the test plants, but the test plants were in the 0.5- to 4-leaf stage and were 5 to 30 cm in height. Eighteen days after application, the herbicidal activity and phytotoxicity were examined. The results are shown in the table below. This test was carried out in a greenhouse through the whole test period.

| Test Compound | Dosage rate of active ingredient (g/a) | Phytotoxicity Soybean | Cotton | Corn | Rice | Herbicidal activity Velvet-leaf | Black night-shade | Barn-yard-grass | Johnson-grass | Giant foxtail |
|---|---|---|---|---|---|---|---|---|---|---|
| (1) | 1.25 | 1 | 1 | 0 | 1 | 3 | 5 | 4 | 4 | 4 |
| | 0.32 | 1 | 0 | 0 | 1 | 3 | 5 | 4 | 4 | 3 |
| (3) | 1.25 | 1 | 1 | 1 | 1 | 3 | 3 | 4 | 4 | 4 |
| | 0.32 | 1 | 1 | 1 | 0 | 3 | 3 | 3 | 4 | 3 |
| (16) | 1.25 | 1 | 1 | 1 | 1 | 4 | 5 | 4 | 5 | 4 |
| | 0.32 | 0 | 1 | 1 | 1 | 4 | 4 | 4 | 4 | 4 |

-continued

| Test Compound | Dosage rate of active ingredient (g/a) | Phytotoxicity | | | | Herbicidal activity | | | | |
|---|---|---|---|---|---|---|---|---|---|---|
| | | Soybean | Cotton | Corn | Rice | Velvet-leaf | Black night-shade | Barn-yard-grass | Johnson-grass | Giant foxtail |
| (28) | 1.25 | 1 | 1 | 0 | 1 | 3 | 4 | 4 | 4 | 4 |
| | 0.32 | 1 | 0 | 0 | 0 | 3 | 3 | 4 | 4 | 4 |
| (43) | 1.25 | 1 | 1 | 1 | 1 | 4 | 5 | 5 | 4 | 4 |
| | 0.32 | 1 | 1 | 0 | 1 | 3 | 5 | 4 | 4 | — |
| C | 1.25 | 0 | 0 | 0 | 0 | 0 | 3 | 2 | 2 | 0 |
| | 0.32 | 0 | 0 | 0 | 0 | 0 | 3 | 1 | 0 | 0 |
| D | 1.25 | 2 | 1 | 2 | 2 | 2 | 2 | 2 | 2 | 0 |
| E | 1.25 | 3 | 2 | 2 | 2 | 1 | 0 | 2 | 3 | 1 |
| | 0.32 | 1 | 1 | 0 | 1 | 0 | 0 | 2 | 3 | 0 |

TEST EXAMPLE 14 FOLIAR TREATMENT TEST IN UPLAND FIELD SOIL

Vats of 33×23 $cm^2$ in area and 11 cm in depth were filled with upland field soil, and seeds of soybean, velvetleaf and sicklepod were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds and crop at that time varied with the kind of the test plants, but the test plants were in the 0.5- to 2-leaf stage and were 5 to 20 cm in height. Eighteen days after application, the herbicidal activity and phytotoxicity were examined. The results are shown in the table below. This test was carried out in a greenhouse through the whole test period.

| Test compound | Dosage rate of active ingredient (g/a) | Phyto-toxicity Soybean | Herbicidal activity | |
|---|---|---|---|---|
| | | | Velvet-leaf | Sicklepod |
| (104) | 0.04 | 0 | 4 | 5 |
| F | 0.16 | 0 | 2 | 1 |
| H | 0.04 | 2 | 3 | 1 |

TEST EXAMPLE 15 FOLIAR TREATMENT TEST IN UPLAND FIELD SOIL

Vats of 33×23 $cm^2$ in area and 11 cm in depth were filled with upland field soil, and seeds of cotton, tall morningglory, sicklepod and black nightshade were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds and crop at that time varied with the kind of the test plants, but the test plants were in the 0.5- to 2.5-leaf stage and were 5 to 15 cm in height. Eighteen days after application, the herbicidal activity and phytotoxicity were examined. The results are shown in the table below. This test was carried out in a greenhouse through the whole test period.

| Test compound | Dosage rate of active ingredient (g/a) | Phyto-toxicity Cotton | Herbicidal activity | | |
|---|---|---|---|---|---|
| | | | Tall morning-glory | Sickle-pod | Black night-shade |
| (122) | 0.08 | 0 | 4 | 5 | 4 |
| (134) | 0.31 | 0 | 4 | 4 | 4 |
| D | 2.5 | 1 | 0 | 0 | 2 |
| E | 2.5 | 3 | 0 | 1 | 3 |

TEST EXAMPLE 16 FOLIAR TREATMENT TEST IN UPLAND FIELD SOIL

Vats of 33×23 $cm^2$ in area and 11 cm in depth were filled with upland field soil, and seeds of cotton, cocklebur and johnsongrass were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds and crop at that time varied with the kind of the test plants, but the test plants were in the 0.5- to 2.5-leaf stage and were 5 to 15 cm in height. Eighteen days after application, the herbicidal activity and phytotoxicity were examined. The results are shown in the table below. This test was carried out in a greenhouse through the whole test period.

| Test compound | Dosage rate of active ingredient (g/a) | Phyto-toxicity Cotton | Herbicidal activity | |
|---|---|---|---|---|
| | | | Cocklebur | Johnson-grass |
| (135) | 0.31 | 0 | 4 | 4 |
| C | 2.5 | 0 | 0 | 2 |
| F | 2.5 | 0 | 0 | 2 |

TEST EXAMPLE 17 FOLIAR TREATMENT TEST IN UPLAND FIELD SOIL

Vats of 33×23 $cm^2$ in area and 11 cm in depth were filled with upland field soil, and seeds of corn, velvetleaf and sicklepod were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds and crop at that time varied with the kind of the test plants, but the test plants were in the 0.5- to 4-leaf stage and were 5 to 30 cm in height. Eighteen days after application, the herbicidal activity and phytotoxicity were examined. The results are shown in the table below. This test was carried out in a greenhouse through the whole test period.

| Test compound | Dosage rate of active ingredient (g/a) | Phytotoxicity Corn | Herbicidal activity Velvetleaf | Herbicidal activity Sicklepod |
|---|---|---|---|---|
| (88) | 0.16 | 0 | 4 | 4 |
| (104) | 0.63 | 0 | 4 | 5 |
| (105) | 0.63 | 0 | 5 | 5 |
| (118) | 0.63 | 0 | 5 | 5 |
| D | 2.5 | 2 | 3 | 0 |
| E | 2.5 | 3 | 1 | 1 |
| F | 2.5 | 0 | 3 | 2 |

TEST EXAMPLE 18 FOLIAR TREATMENT TEST IN UPLAND FIELD SOIL

Vats of 33×23 $cm^2$ in area and 11 cm in depth were filled with upland field soil, and seeds of corn and johnsongrass were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weed and crop at that time varied with the kind of the test plants, but the test plants were in the 2- to 4-leaf stage and were 10 to 30 cm in height. Eighteen days after application, the herbicidal activity and phytotoxicity were examined. The results are shown in the table below. This test was carried out in a greenhouse through the whole test period.

| Test compound | Dosage rate of active ingredient (g/a) | Phytotoxicity Corn | Herbicidal activity Johnsongrass |
|---|---|---|---|
| (62) | 0.08 | 0 | 4 |
| (121) | 0.08 | 0 | 4 |
| (134) | 0.08 | 0 | 4 |
| G | 0.16 | 1 | 2 |

TEST EXAMPLE 19 FOLIAR TREATMENT TEST IN UPLAND FIELD SOIL

Vats of 33×23 $cm^2$ in area and 11 cm in depth were filled with upland field soil, and seeds of corn, velvetleaf, sicklepod and black nightshade were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds and crop at that time varied with the kind of the test plants, but the test plants were in the 0.5- to 4-leaf stage and were 5 to 30 cm in height. Eighteen days after application, the herbicidal activity and phytotoxicity were examined. The results are shown in the table below. This test was carried out in a greenhouse through the whole test period.

| Test compound | Dosage rate of active ingredient (g/a) | Phytotoxicity Corn | Herbicidal activity Velvetleaf | Herbicidal activity Sicklepod | Herbicidal activity Black nightshade |
|---|---|---|---|---|---|
| (122) | 0.02 | 0 | 4 | 5 | 4 |
| (123) | 0.02 | 0 | 4 | 4 | 4 |
| C | 0.16 | 0 | 0 | 0 | 2 |
| H | 0.04 | 0 | 3 | 1 | 2 |

TEST EXAMPLE 20 SOIL TREATMENT TEST IN UPLAND FIELD SOIL

Vats of 33×23 $cm^2$ in area and 11 cm in depth were filled with upland field soil, and seeds of wheat, pale smartweed, birdseye speedwell, field pansy, downy brome, wild oat, blackgrass and annual bluegrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in the table below.

| Test Compound | Dosage rate of active ingredient (g/a) | Phytotoxicity Wheat | Herbicidal activity Pale smartweed | Birdseye speedwell | Field pansy | Downy brome | Wild oat | Blackgrass | Annual bluegrass |
|---|---|---|---|---|---|---|---|---|---|
| (1) | 0.63 | 0 | 3 | 4 | 4 | 4 | 3 | 4 | 4 |
| (14) | 0.63 | 0 | 4 | 4 | 4 | 4 | 3 | 4 | 4 |
| (42) | 0.63 | 1 | 4 | 5 | 4 | 5 | 4 | 4 | 4 |
| | 0.16 | 0 | 3 | 4 | 3 | 4 | 3 | 3 | 4 |
| (43) | 0.63 | 1 | 3 | 5 | 5 | 5 | 4 | 4 | 4 |
| | 0.16 | 0 | 3 | 5 | 4 | 5 | 4 | 4 | 4 |
| (44) | 0.63 | 0 | 4 | 4 | 4 | 5 | 4 | 4 | 4 |
| | 0.16 | 0 | 3 | 4 | 3 | 4 | 3 | 3 | 4 |
| (45) | 0.63 | 0 | 4 | 4 | 4 | 4 | 3 | 4 | 4 |
| | 0.16 | 0 | 3 | 4 | 3 | 4 | 3 | 3 | 4 |
| (56) | 0.63 | 1 | 4 | 5 | 5 | 5 | 4 | 4 | 4 |
| | 0.16 | 1 | 3 | 5 | 3 | 4 | 4 | 4 | 4 |
| (58) | 0.63 | 1 | 4 | 5 | 4 | 5 | 4 | 4 | 4 |
| | 0.16 | 0 | 4 | 5 | 3 | 5 | 4 | 4 | 4 |

-continued

| Test Compound | Dosage rate of active ingredient (g/a) | Phytotoxicity Wheat | Herbicidal activity Pale smart-weed | Birdseye speed-well | Field pansy | Downy brome | Wild oat | Black-grass | Annual blue-grass |
|---|---|---|---|---|---|---|---|---|---|
| C | 0.63 | 1 | 0 | 0 | 0 | 0 | 0 | 3 | 3 |
| D | 0.63 | 0 | 0 | 0 | 0 | 0 | 0 | 0 | 2 |
| E | 0.63 | 3 | 3 | 4 | 4 | 3 | 3 | 4 | 4 |
| | 0.16 | 1 | 2 | 3 | 3 | 1 | 1 | 2 | 2 |

TEST EXAMPLE 21 SOIL TREATMENT TEST IN UPLAND FIELD SOIL

Vats of 33×23 $cm^2$ in area and 11 cm in depth were filled with upland field soil, and seeds of beet and birdseye speedwell were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in the table below.

| Test compound | Dosage rate of active ingredient (g/a) | Phytotoxicity Beet | Herbicidal activity Birdseye speedwell |
|---|---|---|---|
| (1) | 0.31 | 0 | 4 |
| (31) | 0.63 | 0 | 5 |
| (88) | 0.31 | 0 | 4 |
| (137) | 0.31 | 0 | 4 |
| (150) | 0.31 | 0 | 4 |
| C | 1.25 | 2 | 0 |
| D | 2.5 | 2 | 2 |
| G | 0.63 | 0 | 0 |

TEST EXAMPLE 22 SOIL TREATMENT TEST IN UPLAND FIELD SOIL

Vats of 33×23 $cm^2$ in area and 11 cm in depth were filled with upland field soil, and seeds of beet, blackgrass and annual bluegrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in the table below.

| Test compound | Dosage rate of active ingredient (g/a) | Phytotoxicity Beet | Herbicidal activity Blackgrass | Annual bluegrass |
|---|---|---|---|---|
| (150) | 0.31 | 0 | 4 | 4 |
| H | 0.31 | 3 | 3 | 0 |

TEST EXAMPLE 23 SOIL TREATMENT TEST IN UPLAND FIELD SOIL

Vats of 33×23 $cm^2$ in area and 11 cm in depth were filled with upland field soil, and seeds of beet and pale smartweed were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in the table below.

| Test compound | Dosage rate of active ingredient (g/a) | Phytotoxicity Beet | Herbicidal activity Pale smartweed |
|---|---|---|---|
| (77) | 0.63 | 0 | 4 |
| (150) | 0.31 | 0 | 4 |
| E | 0.31 | 3 | 3 |
| F | 1.25 | 2 | 3 |

TEST EXAMPLE 24 SOIL TREATMENT TEST IN UPLAND FIELD SOIL

Vats of 33×23 $cm^2$ in area and 11 cm in depth were filled with upland field soil, and seeds of beet and cleavers were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in the table below.

| Test compound | Dosage rate of active ingredient (g/a) | Phytotoxicity Beet | Herbicidal activity Cleavers |
|---|---|---|---|
| (31) | 0.63 | 0 | 5 |
| (134) | 0.31 | 0 | 4 |
| F | 1.25 | 2 | 3 |

TEST EXAMPLE 25 SOIL TREATMENT TEST IN UPLAND FIELD SOIL

Vats of 33×23 $cm^2$ in area and 11 cm in depth were filled with upland field soil, and seeds of wheat, barley and birdseye speedwell were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in the table below.

| Test compound | Dosage rate of active ingredient (g/a) | Phytotoxicity Wheat | Phytotoxicity Barley | Herbicidal activity Birdseye speedwell |
|---|---|---|---|---|
| (1) | 0.31 | 0 | 0 | 4 |
| (14) | 0.63 | 0 | 0 | 4 |
| (31) | 0.16 | 0 | 0 | 5 |
| (88) | 0.31 | 0 | 0 | 4 |
| C | 5 | 3 | 3 | 3 |
| D | 2.5 | 0 | 2 | 2 |
| G | 0.63 | 0 | 0 | 0 |

TEST EXAMPLE 26 FOLIAR TREATMENT TEST IN UPLAND FIELD SOIL

Vats of 33×23 $cm^2$ in area and 11 cm in depth were filled with upland field soil, and seeds of wheat and pale smartweed were sowed in the respective vats and cultivated for 31 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weed and crop at that time varied with the kind of the test plants, but the test plants were in the 2- to 4-leaf stage and were 10 to 25 cm in height. Twenty-five days after application, the herbicidal activity and phytotoxicity were examined. The results are shown in the table below. This test was carried out in a greenhouse through the whole test period.

| Test compound | Dosage rate of active ingredient (g/a) | Phytotoxicity Wheat | Herbicidal activity Pale smartweed |
|---|---|---|---|
| (63) | 0.04 | 0 | 4 |
| (104) | 0.16 | 0 | 4 |
| C | 0.31 | 0 | 0 |
| D | 1.25 | 0 | 0 |
| F | 0.31 | 1 | 0 |
| G | 0.63 | 1 | 2 |

TEST EXAMPLE 27 FOLIAR TREATMENT TEST IN UPLAND FIELD SOIL

Vats of 33×23 $cm^2$ in area and 11 cm in depth were filled with upland field soil, and seeds of wheat and chickweed were sowed in the respective vats and cultivated for 31 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weed and crop at that time varied with the kind of the test plants, but the test plants were in the 2- to 5-leaf stage and were 5 to 25 cm in height. Twenty-five days after application, the herbicidal activity and phytotoxicity were examined. The results are shown in the table below. This test was carried out in a greenhouse through the whole test period.

| Test compound | Dosage rate of active ingredient (g/a) | Phytotoxicity Wheat | Herbicidal activity Chickweed |
|---|---|---|---|
| (134) | 0.31 | 0 | 4 |
| (135) | 0.31 | 0 | 4 |
| C | 0.31 | 0 | 0 |
| D | 1.25 | 0 | 0 |
| E | 2.5 | 3 | 0 |
| F | 0.31 | 1 | 0 |
| G | 0.63 | 1 | 2 |

TEST EXAMPLE 28 SOIL TREATMENT TEST IN UPLAND FIELD SOIL

The herbicidal activity and phytotoxicity of the test plants shown in the table below were examined according to the same way described in Test Example 10.

The results are shown in the table below.

| Test compound | Dosage rate of active ingredient (g/a) | Phytotoxicity Soybean | Phytotoxicity Cotton | Herbicidal activity Black nightshade | Herbicidal activity Barnyardgrass | Herbicidal activity Johnsongrass | Herbicidal activity Giant foxtail |
|---|---|---|---|---|---|---|---|
| (171) | 1.25 | 0 | 0 | 5 | 4 | 5 | 4 |
| C | 1.25 | 0 | 2 | 1 | 1 | 2 | 0 |
| D | 1.25 | 0 | 0 | 1 | 0 | 0 | 1 |

TEST EXAMPLE 29 SOIL TREATMENT TEST IN UPLAND FIELD SOIL

The herbicidal activity and phytotoxicity of the test plants shown in the table below were examined according to the same way described in Test Example 10.

The results are shown in the table below.

| Test compound | Dosage rate of active ingredient (g/a) | Phytotoxicity Cotton | Herbicidal activity Velvetleaf | Herbicidal activity Black nightshade | Herbicidal activity Barnyardgrass | Herbicidal activity Johnsongrass | Herbicidal activity Giant foxtail |
|---|---|---|---|---|---|---|---|
| (172) | 1.25 | 0 | 4 | 5 | 5 | 4 | 5 |
| C | 1.25 | 2 | 0 | 1 | 1 | 2 | 0 |
| D | 1.25 | 0 | 0 | 1 | 0 | 0 | 1 |

TEST EXAMPLE 30 FOLIAR TREATMENT TEST IN UPLAND FIELD SOIL

The herbicidal activity and phytotoxicity of the test plants shown in the table below were examined according to the same way described in Test Example 15.

The results are shown in the table below.

| Test Compound | Dosage rate of active ingredient (g/a) | Phytotoxicity Cotton | Herbicidal activity Velvet-leaf | Sickle-pod | Black nightshade | Barnyard-grass | Johnson-grass | Giant foxtail |
|---|---|---|---|---|---|---|---|---|
| (172) | 0.04 | 1 | 4 | 4 | 4 | 4 | 5 | 4 |
| C | 0.16 | 0 | 0 | 0 | 2 | 0 | 0 | 0 |
| F | 0.16 | 0 | 2 | 1 | 2 | 0 | 0 | 0 |
| H | 0.04 | 0 | 3 | 1 | 2 | 0 | 2 | 0 |

What is claimed is:

1. A pyrimidine derivative having the formula, (I)

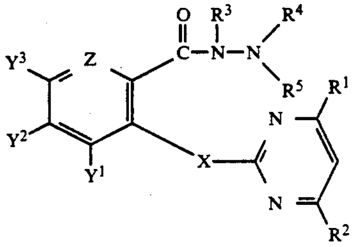

wherein each of $R^1$ and $R^2$, which may be the same or different, is $C_1$-$C_6$ alkyl, $C_1$-$C_6$ alkoxy, halo $C_1$-$C_6$ alkoxy or halogen;

$R^3$ is hydrogen, $C_1$-$C_6$ alkyl, phenyl or phenyl substituted with at least one member selected from the group consisting Of $C_1$-$C_6$ alkyl, $C_1$-$C_6$ alkoxy, halo $C_1$-$C_6$ alkyl, $C_1$-$C_6$ alkoxycarbonyl, nitro and halogen;

each of $R^4$ and $R^5$, which may be the same or different, is hydrogen, $C_1$-$C_6$ alkyl, halo $C_1$-$C_6$ alkyl, phenyl, phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl, nitro and halogen, benzyl, pyridyl, pyridyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl, nitro and halogen, quinolinyl, quinolinyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl, nitro and halogen, $C_1$-$C_6$ alkylcarbonyl, $C_1$-$C_6$ alkoxycarbonyl, and

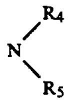

may be N

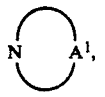

wherein $A^1$ is $C_4$-$C_7$ alkylene, $C_4$-$C_7$ alkylene substituted with $C_1$-$C_6$ alkyl, a group of the formula, $(CH_2)_q$—$A^2$—$(CH_2)_r$—, wherein $A^2$ is S, O,

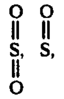

$NR^9$,

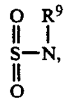

wherein $R^9$ is hydrogen, $C_1$-$C_6$ alkyl, q and r are integer and satisfy the inequalities, $3 \leqq q+r \leqq 6$, $q \geqq 1$, $r \geqq 1$, or a group of the formula, —$(CH_2)_q$—$A^2$—$(CH_2)_r$—, substituted with $C_1$-$C_6$ alkyl wherein q, r and $A^2$ are as defined above; or a group of the formula,

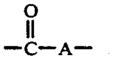

wherein A is $C_2$-$C_4$ alkylene or $C_2$-$C_4$ alkylene substituted with $C_1$-$C_6$ alkyl, Or a group of the formula,

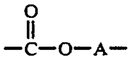

wherein

A is as defined above;

X is oxygen or sulfur;

Z is nitrogen or $CY^4$;

each of $Y^1$, $Y^2$ and $Y^3$, which may be the same or different, is hydrogen, halogen, $C_1$-$C_6$ alkyl or $C_1$-$C_6$ alkoxy; and $Y^4$ is hydrogen, hydroxyl, mercapto, nitro, halogen, $C_1$-$C_6$ alkyl, $C_2$-$C_6$ alkenyl, $C_2$-$C_6$ alkynyl, $C_1$-$C_6$ alkoxy, $C_3$-$C_6$ alkenyloxy, $C_3$-$C_6$ alkynyloxy, halo $C_1$-$C_6$ alkyl, halo $C_2$-$C_6$ alkenyl, halo $C_2$-$C_6$ alkynyl, halo $C_1$-$C_6$ alkoxy, halo $C_3$-$C_6$ alkenyloxy, halo $C_3$-$C_6$ alkynyloxy, $C_1$-$C_6$ alkoxy $C_1$-$C_6$ alkyl, $C_3$-$C_6$ alkenyloxy $C_1$-$C_6$ alkyl, $C_3$-$C_6$ alkynyloxy $C_1$-$C_6$ alkyl, cyano, formyl, carboxyl, $C_1$-$C_6$ alkoxycarbonyl, $C_3$-$C_6$ alkenyloxycarbonyl, $C_3$-$C_6$ alkynyloxycarbonyl, phenyl, phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, phenoxy, phenoxy substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, phenylthio, phenylthio substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen, benzyloxy, benzyloxy substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen, benzylthio, benzylthio substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen,

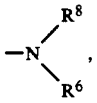, wherein each of $R^8$ and $R^6$, which may be the same or different, is hydrogen, $C_1$–$C_6$ alkyl, $C_3$–$C_6$ alkenyl or $C_3$–$C_6$ alkynyl,

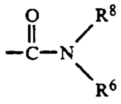, wherein $R^8$ and $R^6$ are as defined above,

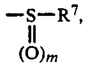

wherein $R^7$ is $C_1$–$C_6$ alkyl, $C_3$–$C_6$ alkenyl or $C_3$–$C_6$ alkynyl and m is an integer of 0, 1 or 2,

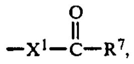

wherein $X^1$ is oxygen or sulfur, and $R^7$ is as defined above, or

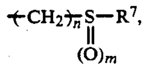

wherein $R^7$ and m are as defined above, and n is an integer from 1 to 4.

2. A pyrimidine derivative according to claim 1, wherein each of $R^1$ and $R^2$, which may be the same or different, is $C_1$–$C_6$ alkoxy.

3. A pyrimidine derivative according to claim 1, wherein both $R^1$ and $R^2$ are methoxy.

4. A pyrimidine derivative accodring to claim 1, wherein Z is nitrogen or $CY^5$ wherein $Y^5$ is hydrogen, halogen, halo $C_1$–$C_6$ alkyl, $C_1$–$C_6$ alkyl, $C_1$–$C_6$ alkoxy, phenyl or phenyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen.

5. A pyrimidine derivative according to claim 1, wherein Z is nitrogen, CH, CF, CCl, CBr or CI.

6. A pyrimidine derivative according to claim 2, wherein Z is CF, CCl, CBr or CI.

7. A pyrimidine derivative according to claim 1, wherein both $Y^1$ and $Y^2$ are hydrogen or fluorine, and $Y^3$ is hydrogen, fluorine or $C_1$–$C_6$ alkoxy.

8. A pyrimidine derivative according to claim 4, wherein both $R^1$ and $R^2$ are methoxy, and X is oxygen.

9. A pyrimidine derivative according to claim 1, wherein it is 3-{2-(4,6-dimethoxypyrimidin-2-yl)oxybenzoyl}amino-2-oxazolidinone of the formula,

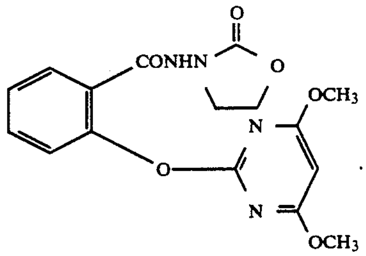

10. A pyrimidine derivative according to claim 1, wherein it is 3-{2-chloro-6-(4,6-dimethoxypyrimidin-2-yl)oxybenzoyl}amino-2-oxazolidinone of the formula,

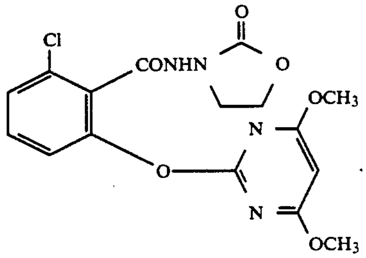

11. A method for producing a pyrimidine derivative which comprises the steps of (i) reacting a carboxylic acid derivative having the formula,

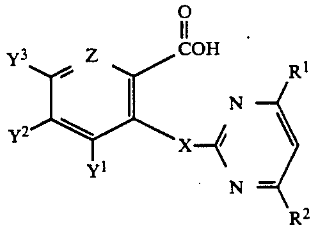

wherein

X is oxygen or sulfur;

Z is nitrogen or $CY^4$;

each of $Y^1$, $Y^2$ and $Y^3$, which may be the same or different, is hydrogen, halogen, $C_1$–$C_6$ alkyl or $C_1$–$C_6$ alkoxy;

$Y^4$ is hydrogen, hydroxyl, mercapto, nitro, halogen, $C_1$–$C_6$ alkyl, $C_2$–$C_6$ alkenyl, $C_2$–$C_6$ alkynyl, $C_1$–$C_6$ alkoxy, $C_3$–$C_6$ alkenyloxy, $C_3$–$C_6$ alkynyloxy, halo $C_1$–$C_6$ alkyl, halo $C_2$–$C_6$ alkenyl, halo $C_2$–$C_6$ alkynyl, halo $C_1$–$C_6$ alkoxy, halo $C_3$–$C_6$ alkenyloxy, halo $C_3$–$C_6$ alkynyloxy, $C_1$–$C_6$ alkoxy $C_1$–$C_6$ alkyl, $C_3$–$C_6$ alkenyloxy $C_1$–$C_6$ alkyl, $C_1$–$C_6$ alkynyloxy $C_1$–$C_6$ alkyl, cyano, formyl, carboxyl, $C_1$–$C_6$ alkoxycarbonyl, $C_3$–$C_6$ alkenyloxycarbonyl, $C_3$–$C_6$ alkynyloxycarbonyl, phenyl, phenyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen, phenoxy, phenoxy substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, phenylthio, phenylthio substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, benzyloxy, benzyloxy substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, benzylthio, benzylthio substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen,

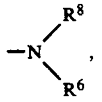

wherein each of $R^8$ and $R^6$, which may be the same or different, is hydrogen, $C_1$-$C_6$ alkyl, $C_3$-$C_6$ alkenyl or $C_3$-$C_6$ alkynyl,

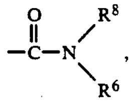

wherein $R^8$ and $R^6$ are as defined above,

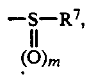

wherein $R^7$ is $C_1$-$C_6$ alkyl, $C_3$-$C_6$ alkenyl or $C_3$-$C_6$ alkynyl and m is an integer of 0, 1 or 2,

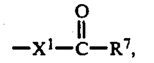

wherein $X^1$ is oxygen or sulfur, and $R^7$ is as defined above, or

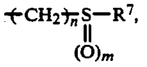

wherein $R^7$ and m are as defined above, and n is an integer of from 1 to 4; and each of $R^1$ and $R^2$, which may be the same or different, is $C_1$-$C_6$ alkyl, $C_1$-$C_6$ alkoxy, halo $C_1$-$C_6$ alkoxy or halogen, with an acid-halogenating agent or an active esterifying agent to obtain a reaction product; and (ii) reacting the reaction product with a hydrazine derivative having the formula,

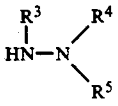

wherein $R^3$ is hydrogen, $C_1$-$C_6$ alkyl, phenyl or phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl, nitro and halogen;

each of $R^4$ and $R^5$, which may be the same or different, is hydrogen, $C_1$-$C_6$ alkyl, halo $C_1$-$C_6$ alkyl, phenyl, phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl, nitro and halogen, benzyl, pyridyl, pyridyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl, nitro and halogen, quinolinyl, quinolinyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl, nitro and halogen, $C_1$-$C_6$ alkylcarbonyl, $C_1$-$C_6$ alkoxycarbonyl, and

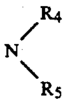

may be

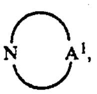

wherein $A^1$ is $C_4$-$C_7$ alkylene, $C_4$-$C_7$ alkylene substituted with $C_1$-$C_6$ alkyl, a group of the formula, $-(CH_2)_q-A^2-(CH_2)_r-$, wherein $A^2$ is S, O,

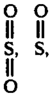

$NR^9$,

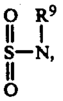

wherein $R^9$ is hydrogen, $C_1$-$C_6$ alkyl, q and r are integer and satisfy the inequalities, $3 \leqq q+r \leqq 6$, $q \geqq 1$, $r \geqq 1$, or a group of the formula, $-(CH_2)_q-A^2-(CH_2)_r-$, substituted with $C_1$-$C_6$ alkyl wherein q, r and $A^2$ are as defined above; or a group of the formula,

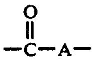

wherein A is $C_2$–$C_4$ alkylene or $C_2$–$C_4$ alkylene substituted with $C_1$–$C_6$, or a group of the formula,

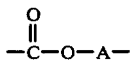

wherein A is as defined above.

12. A herbicidal composition which comprises as an active ingredient a herbicidally effective amount of a pyrimidine derivative having the formula,

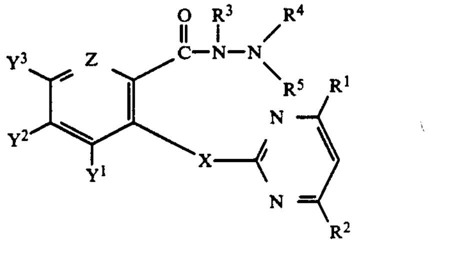

(I)

wherein each of $R^1$ and $R^2$, which may be the same or different, is $C_1$–$C_6$ alkyl, $C_1$–$C_6$ alkoxy, halo $C_1$–$C_6$ alkoxy or halogen:

$R^3$ is hydrogen, $C_1$–$C_6$ alkyl, phenyl or phenyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl, nitro and halogen;

each of $R^4$ and $R^5$, which may be the same or different, is hydrogen, $C_1$–$C_6$ alkyl, halo $C_1$–$C_6$ alkyl, phenyl, phenyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl, nitro and halogen, benzyl, pyridyl, pyridyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl, nitro and halogen, quinolinyl, quinolinyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl, nitro and halogen, $C_1$–$C_6$ alkylcarbonyl, $C_1$–$C_6$ alkoxycarbonyl, and

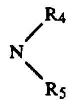

may be

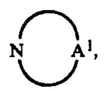

wherein $A^1$ is $C_4$–$C_7$ alkylene, $C_4$–$C_7$ alkylene substituted with $C_1$–$C_6$ alkyl, a group of the formula, $-(CH_2)_q-A^2-(CH_2)_r-$, wherein $A^2$ is S, O,

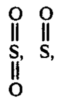

$NR^9$,

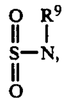

wherein $R^9$ is hydrogen, $C_1$–$C_6$ alkyl, q and r are integer and satisfy the inequalities, $3 \leqq q+r \leqq 6$, $q \geqq 1$, $r \geqq 1$, or a group of the formula, $-(CH_2)_q-A^2-(CH_2)_r-$, substituted with $C_1$–$C_6$ alkyl wherein q, r and $A^2$ are as defined above; or a group of the formula,

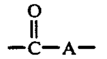

wherein A is $C_2$–$C_4$ alkylene or $C_2$–$C_4$ alkylene substituted with $C_1$–$C_6$ alkyl, or a group of the formula,

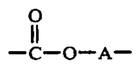

wherein

A is as defined above;

X is oxygen or sulfur;

Z is nitrogen or $CY^4$;

each of $Y^1$, $Y^2$ and $Y^3$, which may be the same or different, is hydrogen, halogen, $C_1$–$C_6$ alkyl or $C_1$–$C_6$ alkoxy; and $Y^4$ is hydrogen, hydroxyl, mercapto, nitro, halogen, $C_1$–$C_6$ alkyl, $C_2$–$C_6$ alkenyl, $C_2$–$C_6$ alkynyl, $C_1$–$C_6$ alkoxy, $C_3$–$C_6$ alkenyloxy, $C_3$–$C_6$ alkynyloxy, halo $C_1$–$C_6$ alkyl, halo $C_2$–$C_6$ alkenyl, halo $C_2$–$C_6$ alkynyl, halo $C_1$–$C_6$ alkoxy, halo $C_3$–$C_6$ alkenyloxy, halo $C_3$–$C_6$ alkynyloxy, $C_1$–$C_6$ alkoxy $C_1$–$C_6$ alkyl, $C_3$–$C_6$ alkenyloxy $C_1$–$C_6$ alkyl, $C_3$–$C_6$ alkynyloxy $C_1$–$C_6$ alkyl, cyano, formyl, carboxyl, $C_1$–$C_6$ alkoxycarbonyl, $C_3$–$C_6$ alkenyloxycarbonyl, $C_3$–$C_6$ alkynyloxycarbonyl, phenyl, phenyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen, phenoxy, phenoxy substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen, phenylthio, phenylthio substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen, benzyloxy, benzyloxy substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl and halogen, benzylthio, benzylthio substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen,

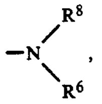

wherein each of $R^8$ and $R^6$, which may be the same or different, is hydrogen, $C_1$-$C_6$ alkyl, $C_3$-$C_6$ alkenyl or $C_3$-$C_6$ alkynyl,

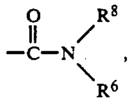

wherein $R^8$ and $R^6$ are as defined above,

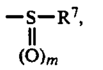

wherein $R^7$ is $C_1$-$C_6$ alkyl, $C_3$-$C_6$ alkenyl or $C_3$-$C_6$ alkynyl and m is an integer of 0, 1 or 2,

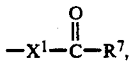

wherein $X^1$ is oxygen or sulfur, and $R^7$ is as defined above, or

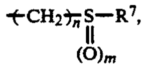

wherein $R^7$ and m are as defined above, and n is an integer of from 1 to 4; and an inert carrier or a diluent.

13. A method for controlling undesirable weeds, which comprises applying the herbicidal composition of claim 12 to an area where undesirable weeds grow or are likely to grow.

* * * * *